(12) United States Patent
Mizuno et al.

(10) Patent No.: US 6,583,296 B2
(45) Date of Patent: Jun. 24, 2003

(54) PYRROLOTHIAZINE AND PYRROLOTHIAZEPINE COMPOUNDS HAVING SEROTONIN-2 RECEPTOR ANTAGONISTIC AND α-1-BLOCKING ACTION

(75) Inventors: Akira Mizuno, Kyoto (JP); Makoto Shibata, Ashikaga (JP); Tomoe Kamei, Takatsuki (JP); Harukazu Fukami, Kyoto (JP); Norio Inomata, Mino (JP)

(73) Assignee: Daiichi Suntory Pharma Co., Ltd., Tokyo (JP)

(*) Notice: Subject to any disclaimer, the term of this patent is extended or adjusted under 35 U.S.C. 154(b) by 0 days.

(21) Appl. No.: 09/939,829

(22) Filed: Aug. 28, 2001

(65) Prior Publication Data

US 2002/0137928 A1 Sep. 26, 2002

Related U.S. Application Data

(62) Division of application No. 09/367,842, filed as application No. PCT/JP98/05955 on Dec. 25, 1998.

(30) Foreign Application Priority Data

Dec. 26, 1997 (JP) .............................. 9-366757

(51) Int. Cl.[7] ............................................ C07D 207/36
(52) U.S. Cl. ...................................... 548/541; 548/568
(58) Field of Search ................................ 548/541, 556

(56) References Cited

U.S. PATENT DOCUMENTS

| 5,206,239 A | 4/1993 | Mizuno et al. |
| 5,391,731 A | 2/1995 | Mizuno et al. |
| 5,397,780 A | 3/1995 | Mizuno et al. |
| 5,399,557 A | 3/1995 | Mizuno et al. |
| 5,416,082 A | 5/1995 | Mizuno et al. |
| 5,684,161 A | 11/1997 | Imoto et al. |
| 5,962,448 A | 10/1999 | Mizuno et al. |
| 6,187,772 B1 | 2/2001 | Mizuno et al. |
| 6,211,362 B1 | 4/2001 | Mizuno et al. |
| 6,258,805 B1 | 7/2001 | Mizuno et al. |
| 6,271,223 B1 | 8/2001 | Mizuno et al. |
| 6,288,056 B1 | 9/2001 | Ogata et al. |

FOREIGN PATENT DOCUMENTS

| EP | 0511 073 | 10/1992 |
| EP | 0 551 527 | 7/1993 |
| EP | 0 557 526 | 9/1993 |
| EP | 0 686 632 | 12/1995 |
| EP | 0 807 632 | 11/1997 |
| HU | 216791 | 11/1995 |

OTHER PUBLICATIONS

Chemical Abstracts, vol. 44, No. 3, Feb. 10, 1950; Abstract No. 1095i, Terent'Ev A P et al: "Sulfonation an sulfonic acids of acidophobic substances. VI. Sulfonation of alpha, alpha'–substituted pyrrole homologs." XP002098315 see abstract & Zhur. Obshchei Khim. (J. Gen. Chem.), vol. 19, 1949, pp. 1365–1369.

Primary Examiner—Robert Gerstl
(74) Attorney, Agent, or Firm—Oblon, Spivak, McClelland, Maier & Neustadt, P.C.

(57) ABSTRACT

A pyrrolesulfonamide compound having the following formula (I):

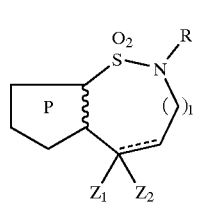

(I)

wherein the ring P represented by

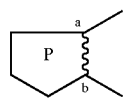

is a pyrrole ring having the following structure:

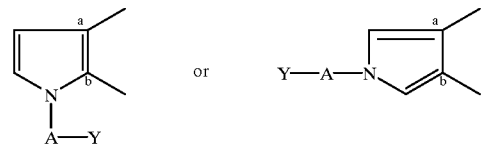

wherein A represents alkylene, alkenylene or alkynylene; and Y represents a group

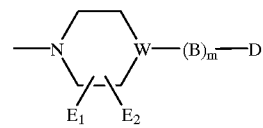

in which W represents CH, C= or N; m stands for 0 or 1 when W is CH or N, or m stands for 1 when W is C=; B represents a specific divalent group; $E_1$ and $E_2$ each independently represents H or lower alkyl; and D represents an aromatic hydrocarbon group or heterocyclic group; l stands for 0 or 1; the dashed line indicates the presence or absence of a bond; and, when the bond is present, $Z_2$ is not present and $Z_1$ represents H but, when the bond is absent, $Z_1$ represents H and $Z_2$ represents OH or $Z_1$ and $Z_2$ are combined together to represent O or a group $NOR_5$, in which $R_5$ represents H, or alkyl, aralkyl or aryl; and R represents H, alkyl, cycloalkyl, cycloalkyl-alkyl or aralkyl. The compound (1) has been improved in potency, selectivity to receptors other than serotonin-2 receptors, toxicity, side effects and/or the like over medicines reported to date and equipped with $\alpha_1$-blocking action and serotonin-2 receptor antagonistic action in combination.

5 Claims, No Drawings

PYRROLOTHIAZINE AND PYRROLOTHIAZEPINE COMPOUNDS HAVING SEROTONIN-2 RECEPTOR ANTAGONISTIC AND α-1-BLOCKING ACTION

This application is a Division of application Ser. No. 09/367,842 Filed on Aug. 26, 1999, allowed, which was filed as International Application PCT/JP98/05955 filed Dec. 25, 1998.

TECHNICAL FIELD

This invention relates to novel pyrrolesulfonamide compounds. More specifically, this invention is concerned with pyrrolo[2,3-e][1,2]thiazine compounds, pyrrolo[3,4-e][1,2]thiazine compounds, pyrrolo[2,3-f][1,2]thiazepine compounds and pyrrolo[3,4-f][1,2]-thiazepine compounds, and salts thereof, said compounds and salts having strong $\alpha_1$-blocking action and serotonin-2 receptor antagonistic action and being useful as pharmaceuticals for the prevention or treatment of hypertension, heart failure, ischemic heart diseases such as angina pectoris, myocardial infarction and post-PTCA restenosis, cerebrovascular disturbances such as cerebral infarction and cerebral sequelae after subarachnoid hemorrhage, peripheral circulatory disturbances such as arteriosclerosis obliterans, thromboangiitis obliterans and Raynaud disease; their preparation processes; and pharmaceuticals containing them as effective ingredients.

BACKGROUND ART

Conventionally, many compounds are known as medicines which act on the circulatory system, including a variety of compounds developed as vasodilators.

Among such vasodilators, $\alpha_1$-blockers represented by prazosin are the subject of a great deal of active development work for their merits in that (1) their antihypertensive action is strong and positive, (2) they give no adverse effect to the metabolism of lipids and carbohydrates and (3) they can be easily used even for hypertensives suffering from complication. Examples of $\alpha_1$-blockers which are clinically used these days can include, in addition to prazosin, bunazosin, tetrazosin, urapidil and doxazosin. Further, medicines equipped with $\alpha_1$-blocking action and anti-serotonin action in combination have possibility to reduce side effects induced by hypotensive action based on the $\alpha_1$-blocking action, such as orthostatic hypotension and reflex tachycardia, and are hence expected to become superior hypertension therapeutics.

Further, hypertensives generally have potentiated platelet-aggregating ability and tend to form thrombi, so that they are considered to develop ischemic heart diseases or peripheral circulatory disturbances. As one of factors which take part in the formation of thrombi, serotonin is known. Serotonin is a compound contained abundantly in platelets, which are a blood component, and in a central nervous system, it acts as a neurotransmitter. In platelets, it is released upon stimulation by thromboxane $A_2$, ADP, collagen or the like, and synergistically acts on release of various platelet aggregation factors through activation of serotonin-2 receptors in the platelets and vascular smooth muscle cells and also on vasoconstriction by norepinephrine through $\alpha_1$ receptors, thereby inducing strong platelet aggregation and vasoconstriction [P.M. Vanhoutte, "Journal of Cardiovascular Pharmacology", Vol. 17 (Supple. 5), S6–S12 (1991)].

Serotonin is also known to potentiate proliferation of vascular smooth muscle cells [S. Araki et al., "Atherosclerosis", Vol. 83, pp.29–34(1990)]. It has been considered that, particularly when endothelial cells are injured as in arteriosclerosis or myocardial infarction, the vasoconstricting action and thrombus forming action of serotonin are exasperated, thereby reducing or even stopping blood supply to myocardial, cerebral and peripheral organs [P. Golino et al., "The New England Journal of Medicine", Vol. 324, No. 10, pp.641–648(1991), Y. Takiguchi et al., "Thrombosis and Haemostasis", Vol. 68(4), pp.460–463 (1992), A. S. Weyrich et al., "American Journal of Physiology", Vol. 263, H349–H358(1992)]. Being attracted by such actions of serotonin or serotonin-2 receptors, various attempts are now under way to use a serotonin-2 receptor antagonist as a pharmaceutical for ischemic diseases of the heart, the brain and peripheral tissues.

With the foregoing in view, medicines which have $\alpha_1$-blocking action and serotonin-2 receptor antagonistic action in combination are expected to have vasodilating action, anti-platelet action and vascular smooth muscle cell proliferation inhibitory action and are considered to become extremely effective medicines for the prevention and treatment of not only hypertension but also all circulator diseases, for example, heart failure, ischemic heart diseases such as angina pectoris, myocardial infarction and post-PTCA restenosis, cerebrovascular disturbances such as cerebral infarction and cerebral sequelae after subarachnoid hemorrhage, peripheral circulatory disturbances such as arteriosclerosis obliterans, thromboangiitis obliterans and Raynaud disease.

To date, several medicines have been reported to have $\alpha_1$-blocking action and serotonin-2 receptor antagonistic action in combination. They are however still accompanied with many problems to be improved in potency, selectivity to other receptors, toxicity, side effects and/or the like. There is accordingly an outstanding demand for the provision of still better compounds.

DISCLOSURE OF THE INVENTION

In view of the foregoing circumstances, the present inventors have proceeded with extensive research toward compounds which have strong $\alpha_1$-blocking action and serotonin-2 receptor antagonistic action in combination and also have low toxicity and less side effects and are thus useful for the prevention and treatment of all circulatory diseases such as hypertension, heart failure, ischemic heart diseases, cerebrovascular disturbances and peripheral circulatory disturbances. As a result, it has been found that pyrrolo[2,3-e]-thiazine compounds, pyrrolo[3,4-e]thiazine compounds, pyrrolo[2,3-f]thiazepine compounds and pyrrolo[3,4-f]-thiazepine compounds can satisfy such conditions.

Incidentally, pharmaceuticals having the pyrrolo[2,3-e]thiazine skeleton, pyrrolo[3,4-e]thiazine skeleton, pyrrolo[2,3-f]thiazepine skeleton or pyrrolo[3,4-f]thiazepine skeleton did not exist in the past, to say nothing of reports even on the synthesis of compounds having these skeletons.

The present invention has been completed based on the above described findings. A first object of the present invention is to provide a pyrrolesulfonamide compound or a salt thereof, said pyrrolesulfonamide compound being represented by the following formula (I):

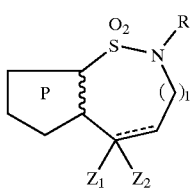

(I)

wherein
the ring P represented by

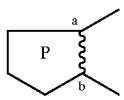

means a pyrrole ring represented by the following structure:

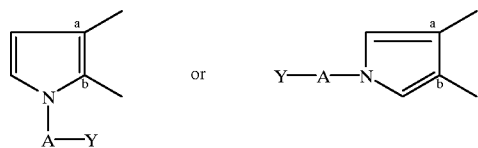

in which A represents a substituted or unsubstituted alkylene group, a substituted or unsubstituted alkenylene group or a substituted or unsubstituted alkynylene group; Y represents a group

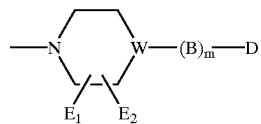

in which W represents CH, C= or a nitrogen atom; and, when W represents CH, m stands for 0 or 1, B represents a carbonyl group, a sulfonyl group, an alkylene group, an alkenylene group, a group —C(OH) $R_1$— in which $R_1$ represents a substituted or unsubstituted aryl group, a group —CHR$_2$— in which $R_2$ represents a substituted or unsubstituted aryl group, or a substituted or unsubstituted cyclic or acyclic acetal group; when W represents C=, m stands for 1, B represents a group

in which the double bond is coupled with W and $R_3$ represents a substituted or unsubstituted aryl group or a substituted or unsubstituted aralkyl group; when W represents a nitrogen atom, m stands for 0 or 1, and B represents a carbonyl group, a sulfonyl group, an alkylene group, an alkenylene group or a group —CHR$_4$— in which $R_4$ represents a substituted or unsubstituted aryl group; $E_1$ and $E_2$ each independently represents a hydrogen atom or a lower alkyl group; and D represents a substituted or unsubstituted aromatic hydrocarbon group or a substituted or unsubstituted aromatic heterocyclic group;

l represents 0 or 1;

the dashed line indicates the presence or absence of a bond; and, when the bond indicated by the dashed line is present, $Z_2$ is not present and $Z_1$ represents a hydrogen atom but, when the bond indicated by the dashed line is absent, $Z_1$ represents a hydrogen atom and $Z_2$ represents a hydroxyl group; or $Z_1$ and $Z_2$ are combined together to represent an oxygen atom or a group NOR$_5$ in which $R_5$ represents a hydrogen atom, a substituted or unsubstituted alkyl group, a substituted or unsubstituted aralkyl group or a substituted or unsubstituted aryl group; and R represents a hydrogen atom, a linear or branched alkyl group, a cycloalkyl group, a cycloalkylalkyl group or a substituted or unsubstituted aralkyl group.

Another object of the present invention is to provide a preparation process of the pyrrolesulfonamide compound (I) or its salt.

A further object of the present invention is to provide a pharmaceutical which comprises the pyrrole-sulfonamide compound (I) or its pharmaceutically-acceptable salt as an effective ingredient and is usable for the treatment or the like of circulatory diseases.

BEST MODES FOR CARRYING OUT THE INVENTION

In the pyrrolesulfonamide compound (I) of the present invention, preferred examples of the group R can include a hydrogen atom; linear or branched alkyl groups having 1–8 carbon atoms preferably, such as methyl, ethyl, n-propyl, isopropyl and n-pentyl; cycloalkyl groups having 3–8 carbon atoms, such as cyclopropyl, cyclopentyl and cyclohexyl; cycloalkylalkyl groups having 4–8 carbon atoms, such as cyclopropylmethyl, cyclohexylmethyl and cyclohexylethyl; and aralkyl groups having 7–22 carbon atoms, such as diphenylmethyl, benzyl and phenethyl. One or more hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy. Particularly preferred examples of the group R can include hydrogen atom, methyl and ethyl.

Further, preferred examples of the group $Z_1$ and the group $Z_2$ in the compound (I) according to the present invention can include the following combinations: when the bond indicated by the dashed line is present, $Z_2$ is not present and $Z_1$ represents a hydrogen atom; when the bond indicated by the dashed line is absent, $Z_1$ represents a hydrogen atom and $Z_2$ represents a hydroxyl group, or $Z_1$ and $Z_2$ are combined together to represent an oxygen atom or a group NOR$_5$.

Preferred examples of $R_5$ in the group NOR$_5$ can include a hydrogen atom; linear or branched alkyl groups having 1–4 carbon atoms preferably, such as methyl and ethyl; aryl groups having 6–14 carbon atoms, such as phenyl and naphthyl; and aralkyl groups having 7–22 carbon atoms, such as benzyl and phenethyl. One or more of the hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy. Of these, hydrogen atom and methyl group are particularly preferred.

Further, the ring P in the pyrrolesulfonamide compound (I) of the present invention represents one of the following pyrrole rings:

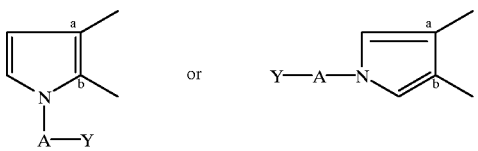

wherein A and Y have the same meanings as defined above. Among these, particularly preferred are pyrrole rings represented by the following formula:

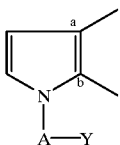

wherein A and Y have the same meanings as defined above.

On the other hand, preferred examples of the group A can include linear or branched alkylene groups having 2–10 carbon atoms, such as ethylene, trimethylene, tetramethylene, pentamethylene and octamethylene; linear or branched alkenylene groups having 4–10 carbon atoms, such as 2-butenylene and 3-pentenylene; and linear or branched alkynylene groups having 4–10 carbon atoms, such as 2-butynylene and 3-pentynylene. One or more of the hydrogen atoms of each of these groups may be substituted by a like number of halogen atoms such as fluorine, chlorine and/or bromine atoms. Among the above groups, trimethylene, tetramethylene and pentamethylene are particularly preferred.

In the ring P, Y is a group

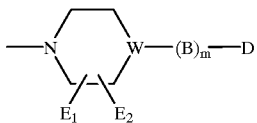

wherein B, D, $E_1$, $E_2$, W and m have the same meanings as defined above. A group represented by the following formula:

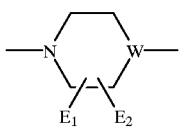

wherein $E_1$, $E_2$ and W have the same meanings as defined above, said group being included in the above group, is a heterocyclic group derived from piperidine or piperazine, and two or less of the hydrogen atoms on the ring may be substituted by a like number of alkyl groups having 1–4 carbon atoms preferably, such as methyl and/or ethyl.

When the above group is a heterocyclic group derived from piperidine, m stands for 0 or 1 (with the proviso that m stands for 1 when W represents C=), and B represents a carbonyl group, a sulfonyl group, an alkylene group (an alkylene group having 1–4 carbon atoms preferably, with a methylene group being particularly preferred), an alkenylene group (an alkenylene group having 2–5 carbon atoms preferably, with a 2-propenylene group being particularly preferred), a group —C(OH)$R_1$— in which $R_1$ is an aryl group having 6–14 carbon atoms, such as phenyl or naphthyl, in which one or more of the hydrogen atoms may be substituted, a group —CHR$_2$— in which $R_2$ is an aryl group having 6–14 carbon atoms, such as phenyl or naphthyl, in which one or more of the hydrogen atoms may be substituted, a group

in which the double bond is coupled with W, $R_3$ represents an aryl group having 6–14 carbon atoms, such as phenyl or naphthyl, or an aralkyl group having 7–22 carbon atoms, such as benzyl or phenethyl, and these groups may be in substituted forms, or a cyclic or acyclic acetal group in which one or more of the hydrogen atoms may be substituted.

Exemplary cyclic or acyclic acetal groups include:

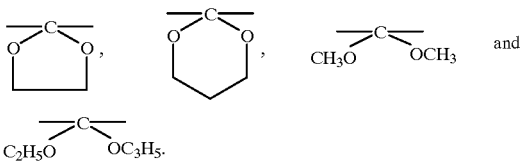

In the above-described definition of B, preferred examples of substituents on the groups $R_1$, $R_2$ and $R_3$ can include one or more alkyl groups having 1–4 carbon atoms, such as methyl and ethyl; aryl groups having 6–14 carbon atoms, such as phenyl and naphthyl; halogen atoms such as fluorine atoms, chlorine atoms and bromine atoms; alkoxy groups having 1–4 carbon atoms, such as methoxy and ethoxy; hydroxyl groups; cyano groups; and nitro groups.

Further, illustrative of substituents on the cyclic or acyclic acetal are halogen atoms such as fluorine atoms, chlorine atoms, and bromine atoms; alkyl groups having 1–4 carbon atoms, such as methyl and ethyl; aryl groups having 6–14 carbon atoms, such as phenyl and naphthyl; aralkyl groups having 7–22 carbon atoms, such as benzyl and phenethyl; and alkylidene groups having 1–4 carbon atoms preferably, such as methylidene and ethylidene.

As a particularly preferred example of B, a carbonyl group can be mentioned.

When the heterocyclic group is a group derived from piperazine, m stands for 0 or 1 (preferably 0), and B represents a carbonyl group, a sulfonyl group, an alkylene group (preferably, an alkylene group having 1–4 carbon atoms, with a methylene group being particularly preferred), an alkenylene group (preferably, an alkenylene group having 3–6 carbon atoms, with a 2-propenylene group being particularly preferred), a group —CHR$_4$— in which $R_4$ represents an aryl group having 6–14 carbon atoms, such as phenyl or naphthyl.

The above-described $R_4$ may be substituted further, for example, by one or more of halogen atoms such as fluorine, chlorine and/or bromine, alkyl groups having 1–4 carbon atoms preferably, such as methyl and/or ethyl, alkoxy groups having 1–4 carbon atoms preferably, such as methoxy and/or ethoxy, nitro groups, cyano groups, carboxyl groups, and/or hydroxyl groups.

As a preferred example of the above-described B, a substituted or unsubstituted phenylmethylene group can be mentioned.

Preferred examples of group D can include aromatic hydrocarbon groups having 6–28 carbon atoms preferably, such as a phenyl group in which one or more of the hydrogen atoms may be substituted and a naphthyl group in which one or more of the hydrogen atoms may be substituted.

Other preferred examples of D can include aromatic heterocyclic groups, preferably those each of which is monocyclic or bicyclic and contains three or less hetero atoms, such as pyridyl, pyrimidinyl, benzisothiazolyl, benzisoxazolyl, indazolyl and indolyl groups in which one or more of hydrogen atoms may be substituted. Examples of the hetero atoms can include oxygen, sulfur and nitrogen atoms.

Examples of the substituents for the above aromatic hydrocarbon group or aromatic heterocyclic group can include halogen atoms such as fluorine, chlorine and bromine; alkyl groups having 1–4 carbon atoms preferably, such as methyl and ethyl; alkoxyl groups having 1–4 carbon atoms preferably, such as methoxy and ethoxy; aryl groups having 6–14 carbon atoms, such as phenyl and naphthyl; aralkyl groups having 7–22 carbon atoms, such as benzyl and phenethyl; aralkyloxy groups having 7–22 carbon atoms preferably, such as benzyloxy; cyano groups; nitro groups; carboxyl groups; alkoxycarbonyl groups (with an alcohol moiety thereof having 1–6 carbon atoms preferably); lower alkylsulfonylamino groups (with an alkyl moiety thereof having 1–4 carbon atoms preferably); carbamoyl groups; and hydroxyl groups.

Among these examples of group D, preferred ones can include phenyl groups which may be unsubstituted or substituted by one or more of halogen atoms, alkoxy groups and/or hydroxyl groups; benzisothiazolyl groups which may be unsubstituted or substituted by one or more halogen atoms; benzisoxazolyl groups which may be unsubstituted or substituted by one or more halogen atoms; and indazolyl groups which may be unsubstituted or substituted by one or more halogen atoms. Particularly preferred are an unsubstituted phenyl group; and phenyl groups substituted by one or more of fluorine atoms, methoxy groups and/or hydroxyl groups.

Many of the compounds (I) according to the present invention have isomers. It is to be noted that these isomers and mixtures thereof are all embraced by the present invention.

The pyrrolesulfonamide compounds (I) according to the present invention can be prepared by various processes. It is however preferred to prepare each of them, for example, by using a pyrrolesulfonamide compound (II) or (II'), which is available by Process 1 to be described below, and following any one of the processes to be described as Process 2 onwards.

Process 1

Pyrrolesulfonamide compounds (II) and (II') useful as starting materials can be synthesized, for example, by the following process:

Compounds represented by the formula (II) and (II') can be obtained in accordance with the following reaction scheme, namely, by converting pyrrole-3-sulfonic acid or a salt thereof represented by the formula (XIII) into a pyrrole-3-sulfonyl halide represented by the formula (XIV), reacting α-aminoacetic acid, β-aminopropionic acid or a derivative thereof (XV) or an organic or inorganic acid salt thereof with the compound (XIV) and, if necessary, conducting deprotection to obtain a compound represented by the formula (XVI) and then subjecting the thus-obtained compound to a ring-closing reaction.

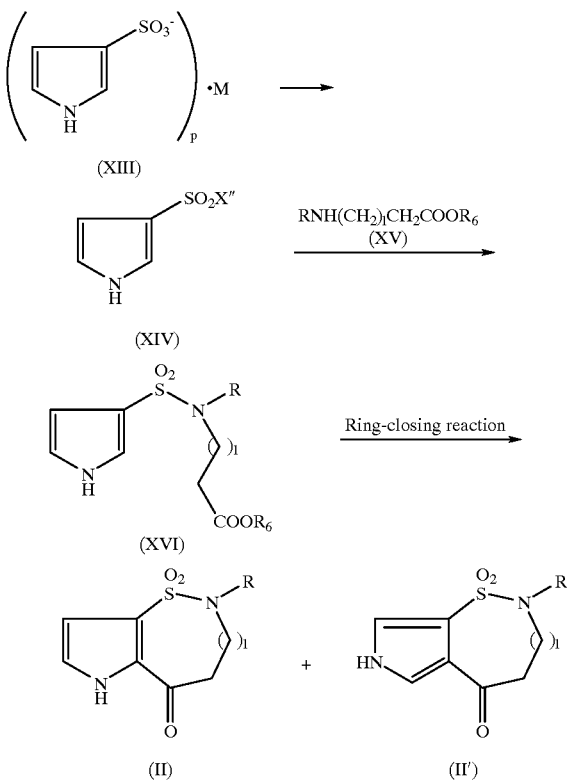

wherein M represents a hydrogen ion, an alkali metal ion, an alkaline earth metal ion or a quaternary ammonium ion, and p stands for 1 when M represents a hydrogen ion, an alkali metal ion or a quaternary ammonium ion or p stands for 2 when M represents an alkaline earth metal ion, X" represents a chlorine atom or a bromine atom, $R_6$ represents a hydrogen atom or a carboxyl-protecting group, and R and l have the same meanings as defined above.

Illustrative of M in the compound represented by the formula (XIII) in the above scheme are hydrogen ion; alkali metal ions such as sodium ion and potassium ion; alkaline earth metal ions such as barium ion; and quaternary ammonium ions such as pyridinium ion. The compound represented by the formula (XIII) can be obtained in accordance with the following formula, namely, by causing a sulfonating agent such as sulfur trioxide.pyridine complex to act on pyrrole (XVII) and, if necessary, treating the resultant compound with an acid such as hydrochloric acid or sulfuric acid or a base such as sodium hydroxide, sodium carbonate, sodium hydrogencarbonate or barium hydroxide.

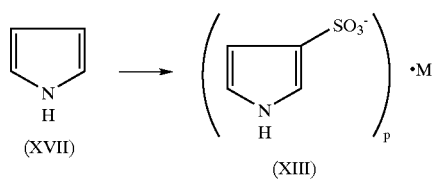

wherein M and p have the same meanings as defined above.

Further, the compound (XIV) can be obtained by causing phosphorus pentachloride or phosphorus pentabromide to act on the compound (XIII) in a solvent which does not take part in the reaction, such as ethyl ether or toluene. In addition, as the carboxyl-protecting group represented by the group $R_6$ in the compound (XV), it is possible to use, in addition to lower alkyl groups such as methyl, ethyl, n-propyl, isopropyl, n-butyl, isobutyl and t-butyl and aralkyl groups having 7–20 carbon atoms, such as benzyl and 9-anthrylmethyl, conventional protecting groups such as those described in T. W. Greene: "Protective Groups in organic Synthesis" (John Wiley & Sons, Inc.) and the like.

Further, as an illustrative synthesis process of the compound (XVI), a process can be mentioned in which a base is added to the compound (XIV), as needed, and α-aminoacetic acid, β-aminopropionic acid or a derivative thereof (XV) or an organic or inorganic acid salt thereof is caused to act. Usable examples of the base can include organic bases such as triethylamine and pyridine, and inorganic bases such as sodium hydrogen-carbonate, potassium carbonate and sodium hydroxide.

The compound (XVI) so obtained is subjected to a cyclizing reaction, optionally after removing the protecting group by virtue of a suitable method such as the action of an acid or a base, or catalytic reduction. This cyclizing reaction is conducted by treating the compound (XVI) together with an organic acid such as methanesulfonic acid, an inorganic acid such as sulfuric acid or polyphosphoric acid or a mixture of such an organic or inorganic acid and phosphorus pentoxide at room temperature to 170° C., preferably at 80–120° C. In this case, a solvent which does not take part in the reaction may be added as needed.

Further, the cyclizing reaction can also be practiced by, optionally after addition of a catalyst such as dimethylformamide to the compound (XVI) in which $R_6$ is a hydrogen atom, treating the compound with oxalyl chloride, thionyl chloride, thionyl bromide, oxalyl bromide, phosgene, phosphorus trichloride, phosphorus tribromide, phosphoryl chloride, phosphoryl bromide or the like to convert it into its corresponding acid halide and then treating the acid halide at −20° C. to reflux temperature in the presence of a Lewis acid such as aluminum chloride, aluminum bromide, boron trifluoride-ether complex or tin tetrachloride in a solvent such as dichloromethane, 1,2-dichloroethane or nitromethane. In the above-described reactions, the compound (II) and the compound (II') can be formed at varied ratios by changing the reaction conditions.

Process 2

Among the pyrrolesulfonamide compounds (I), compounds (Ia) and (Ia') in each of which $Z_1$ and $Z_2$ are combined together to represent an oxygen atom can be synthesized, for example, by any one of the following processes.

Process (a)

Each compound (Ia) or compound (Ia') can be obtained in accordance with the following reaction scheme, namely, by reacting a compound represented by the formula (II) or (II') with a compound represented by the formula (III) to convert the compound (II) or (II') into a compound represented by the formula (IV) or (IV') and then reacting a nitrogen-containing compound represented by the formula (V) or a salt thereof with the compound (IV) or (IV').

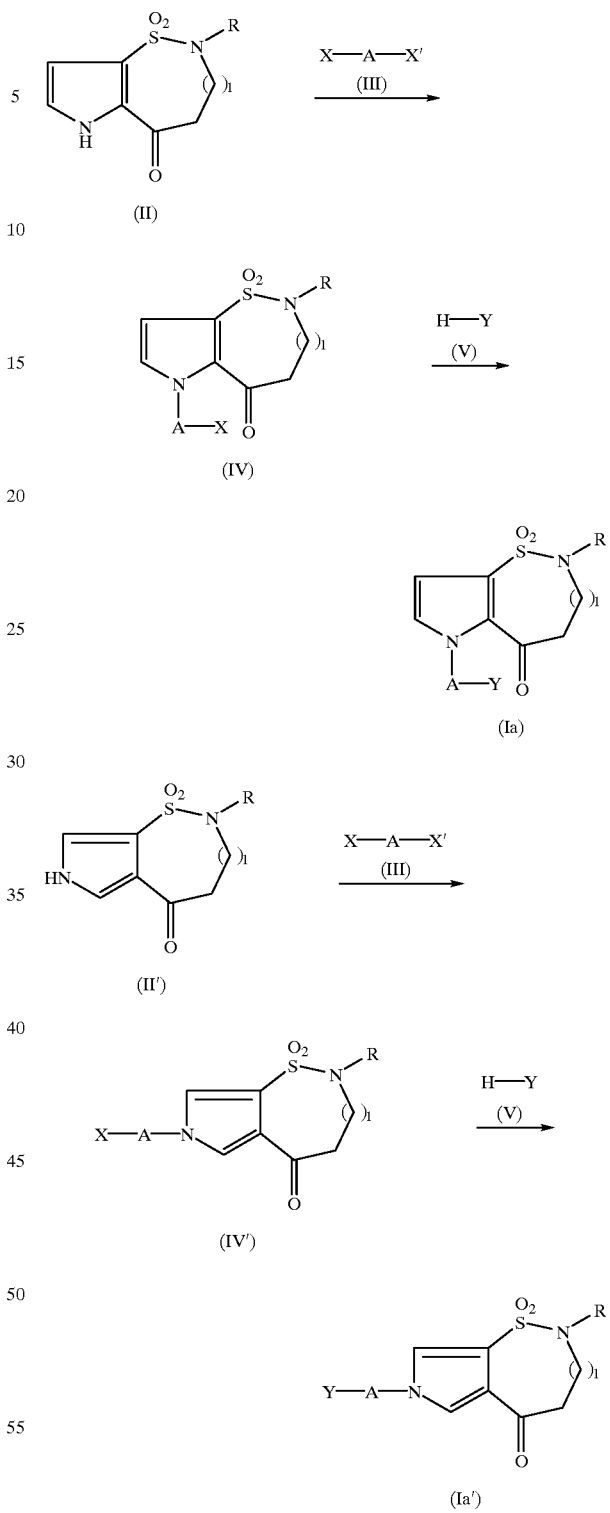

wherein A, R, Y and l have the same meanings as defined above, and X and X' represent the same or different eliminative groups.

In the above-described reaction, the conversion from the compound (II) or (II') into the compound (IV) or (IV') can be effected by treating the compound (II) or (II') with an organic or inorganic base and then reacting the compound (III), or by causing the compound (III) to act on the compound (II) or (II') in the presence of such a base.

The groups X and X' in the compound (III) are eliminative groups, and illustrative can be halogen atoms such as chlorine and bromine, alkylsulfonyloxy groups such as methanesulfonyloxy, and arylsulfonyloxy groups such as p-toluenesulfonyloxy.

Exemplary inorganic bases or organic bases can include sodium carbonate, potassium carbonate, sodium hydroxide, potassium hydroxide, sodium hydride, triethylamine, sodium ethoxide, and potassium t-butoxide. Further, illustrative of a solvent usable in this reaction are acetone, 2-butanone, acetonitrile, dimethyl sulfoxide, dioxane, and toluene. The reaction can be conducted at −20° C. to reflux temperature.

To prepare the compound (Ia) or (Ia') from the thus-obtained compound (IV) or (IV'), it is only necessary to react the compound (IV) or (IV') and the nitrogen-containing compound (V) or an organic acid salt or inorganic acid salt thereof, optionally together with an organic base such as triethylamine, pyridine, collidine or potassium t-butoxide or an inorganic base such as potassium carbonate, sodium carbonate, sodium hydrogencarbonate, potassium hydroxide or sodium hydroxide and optionally with the addition of an alkali iodide such as potassium iodide or sodium iodide, in a solventless manner or in the above-exemplified solvent or a solvent such as methanol or ethanol at room temperature to 150° C.

Examples of the nitrogen-containing compound (V) can include 1-phenylpiperazine, 1-(2-fluorophenyl)piperazine, 1-(3-fluorophenyl)piperazine, 1-(4-fluorophenyl)piperazine, 1-(4-hydroxyphenyl)piperazine, 1-(2-chlorophenyl) piperazine, 1-(3-chlorophenyl)piperazine, 1-(4-chlorophenyl)piperazine, 1-(2-methoxyphenyl)piperazine, 1-(3-methoxyphenyl)piperazine, 1-(4-methoxyphenyl) piperazine, 1-(4-methanesulfonamidophenyl)piperazine, 1-(4-cyanophenyl)piperazine, 1-(4-carbamoylphenyl) piperazine, 1-(4-methoxycarbonylphenyl)piperazine, 1-(2-pyridyl)piperazine, 1-(2-pyrimidinyl)piperazine, 1-benzylpiperazine, 1-diphenylmethylpiperazine, 1-cinnamylpiperazine, 1-benzoylpiperazine, 1-(4-benzyloxybenzoyl)piperazine, 1-(4-hydroxybenzoyl) piperazine, 1-(2-furoyl)piperazine, 1-(1,2-benzisoxazol-3-yl)piperazine, 1-(1,2-benzisothiazol-3-yl)piperazine, 4-phenylpiperidine, 4-benzylpiperidine, α,α-bis(4-fluorophenyl)-4-piperidine-methanol, 4-(4-fluorobenzoyl) piperidine, 4-benzoylpiperidine, 4-(4-methoxybenzoyl) piperidine, 4-(4-chlorobenzoyl)piperidine, 4-(6-fluoro-1,2-benzisoxazol-3-yl)piperidine, 4-(6-fluoro-1,2-benzisothiazol-3-yl)piperidine, 4-(6-fluoro-1H-indazol-3-yl)piperidine, 4-[(4-fluorophenyl)sulfonyl]piperidine, 4-[bis (4-fluorophenyl)methylene]piperidine, and 4-(4-fluorobenzoyl)piperidine ethylene acetal. These compounds are either known in the art or readily available by processes known per se in the art or by processes similar to such known processes.

Process (b)

Further, the compound (Ia) or (Ia') can also be obtained by causing a nitrogen-containing compound represented by the formula (VI) to act on the compound represented by the formula (II) or (II') in accordance with the following reaction formula:

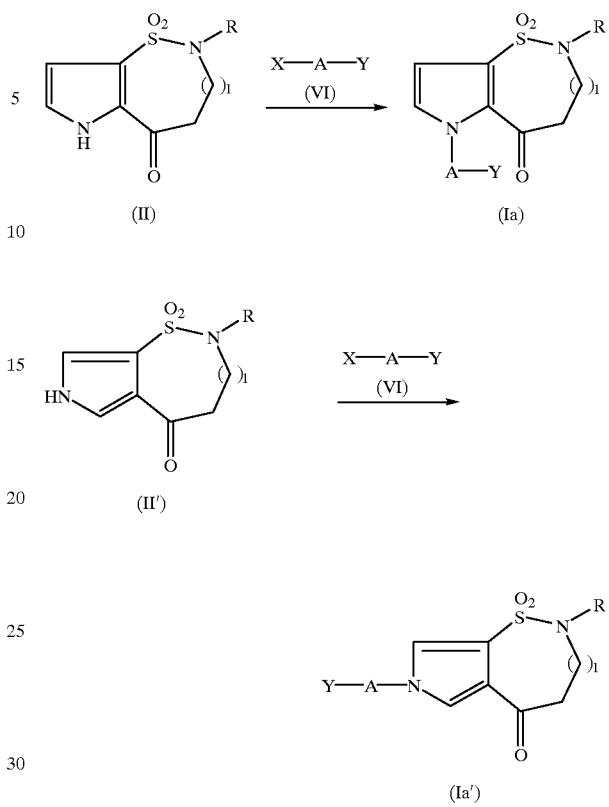

wherein A, R, X, Y and l have the same meanings as defined above.

The conversion from the compound (II) or (II') into the compound (Ia) or (Ia') is conducted by causing the compound (VI) to act either after treatment of the compound (II) or (II') with an inorganic base or an organic base or in the presence of an inorganic base or an organic base. Reaction conditions are similar to those employed upon conversion from the compound (II) into the compound (IV) and described above under Process (a) of Process 2. Further, the compound (VI) can be synthesized by reacting the compound (III) with the compound (V) in a manner known per se in the art.

Process 3

Among the pyrrolesulfonamide compounds (I), the compounds (Ic) and (Ic') and the compounds (Ie) and (Ie') in each of which $Z_1$ and $Z_2$ are combined together to represent a group $NOR_5$ can each be synthesized by any one of the following processes.

Process (a)

Each compound (Ie) or (Ie') is obtained in accordance with the following reaction scheme, namely, by causing hydroxylamine or a derivative thereof (VII) or a salt thereof to act on a compound represented by the formula (IV) or (IV') and then causing a nitrogen-containing compound (V) to act.

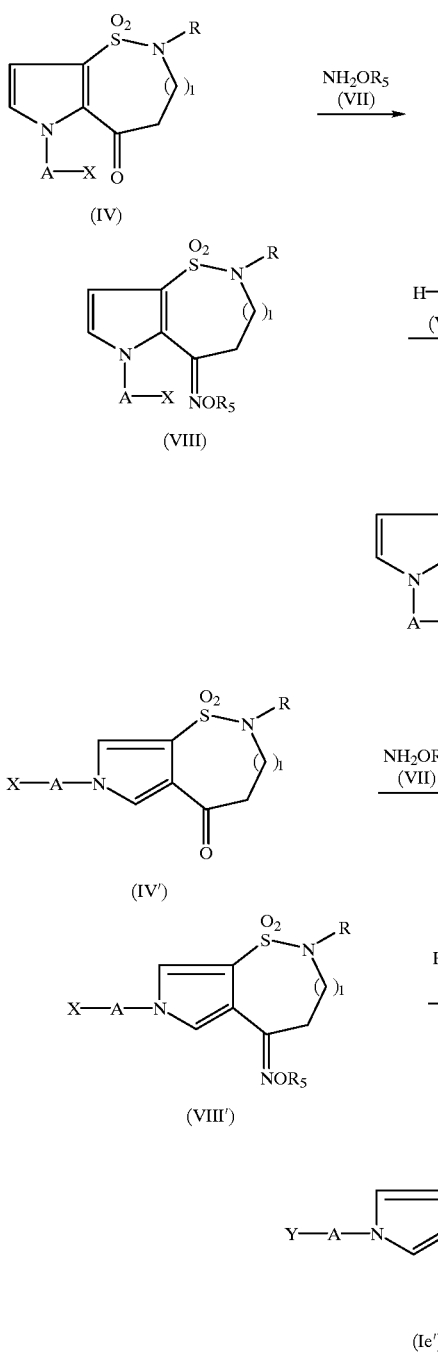

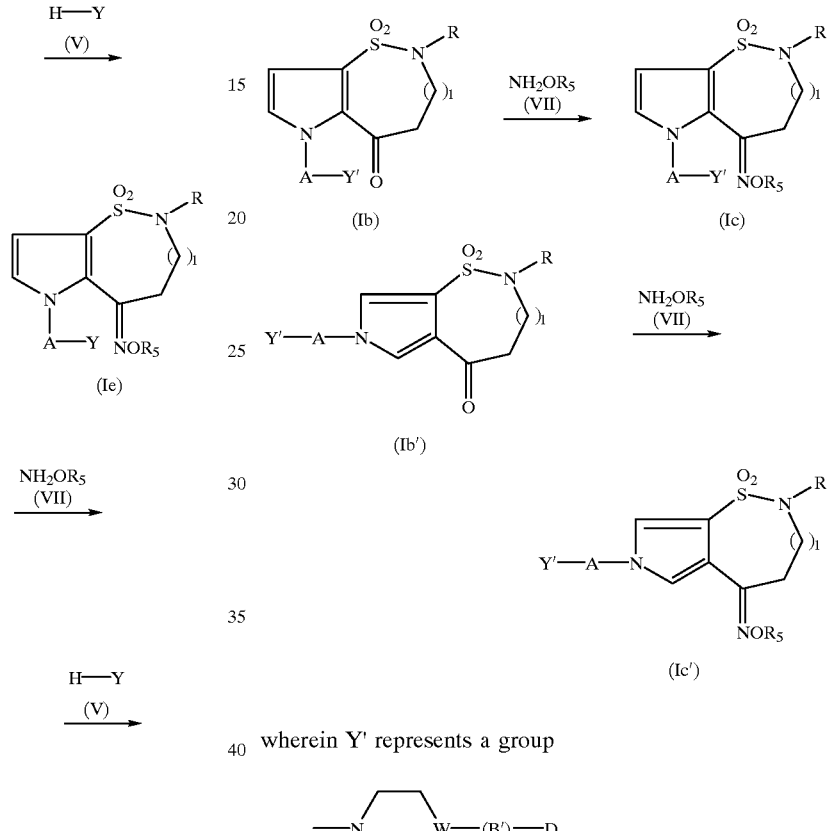

wherein A, R, $R_5$, X, Y and l have the same meanings as defined above.

The reaction between the compound (IV) or (IV') and the hydroxylamine or its derivative (VII) is effected, if necessary, in the presence of an organic base such as pyridine, triethylamine, collidine or sodium acetate or an inorganic base such as potassium carbonate or sodium hydroxide. The hydroxylamine or its derivative (VII) may also be used in the form of an organic acid salt or an inorganic acid salt.

The reaction is conducted at 0° C. to reflux temperature, preferably 0° C.–100° C. by adding a suitable solvent, for example, methanol, ethanol, propanol, tetrahydrofuran, dimethylformamide or dimethylsulfoxide as needed.

Further, the conversion from the thus-obtained compound (VIII) or (VIII') into the compound (Ie) or (Ie') can be effected under similar conditions as in the conversion from the compound (IV) into the compound (Ia) shown above under Process (a) of Process 2.

Process (b)

Each compound (Ic) or (Ic') is obtained by causing hydroxylamine or its derivative (VII) or a salt thereof to act on a compound (Ib) or (Ib') in accordance with the following reaction formula.

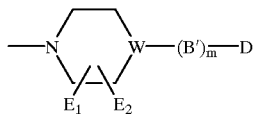

wherein Y' represents a group

in which when W represents CH, B' represents a sulfonyl group, an alkylene group, an alkenylene group, a group —C(OH)R$_1$— in which R$_1$ represents a substituted or unsubstituted aryl group, a group —CHR$_2$— in which R$_2$ represents a substituted or unsubstituted aryl group, or a substituted or unsubstituted cyclic or acyclic acetal group; when W represents C═, B' represents a group in which the double bond is coupled with W and R$_3$ represents a substituted or unsubstituted aryl group or a substituted or unsubstituted aralkyl group; when W represents a nitrogen atom, B' represents a carbonyl group, a sulfonyl group, an alkylene group, an alkenylene group or a group —CHR$_4$— in which R$_4$ represents a substituted or unsubstituted aryl group; and D, E$_1$, E$_2$ and m have the same meanings as defined above, and A, R, $R_5$ and l have the same meanings as defined above.

The conversion from the compound (Ib) or (Ib') into the compound (Ic) or (Ic') can be effected under similar conditions as the conversion from the compound (IV) into the compound (VIII) shown above under Process (a) of Process 3.

Process 4

Among the pyrrolesulfonamide compounds (I), the compounds (Id) and (Id') and the compounds (If) and (If') in each of which $Z_1$ represents a hydrogen atom and $Z_2$ represents a hydroxyl group can each be synthesized by any one of the following processes.

Process (a)

Each compound (If) or (If') is obtained in accordance with the following reaction scheme, namely, by reducing a compound represented by the formula (IV) or (IV') and then causing a nitrogen-containing compound (V) to act.

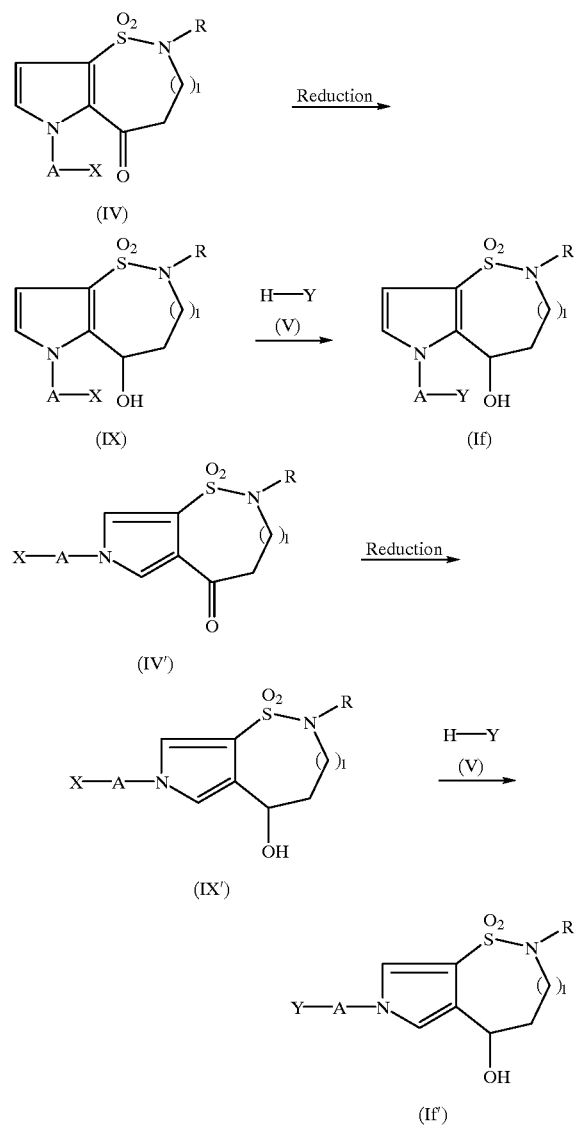

wherein A, R, X, Y and l have the same meanings as defined above.

The conversion from the compound (IV) or (IV') into the compound (IX) or (IX') is conducted by treating the compound represented by the formula (IV) or (IV') with a reducing agent such as sodium borohydride, potassium borohydride or sodium cyanoborohydride at −78° C. to reflux temperature, preferably −20° C. to room temperature in a conventionally used solvent.

The conversion from the compound (IX) or (IX') into the compound (If) or (If') can be effected under similar conditions as the conversion from the compound (IV) into the compound (Ia) shown above under Process (a) of Process 2.

Process (b)

Each compound (Id) or (Id') is obtained by reducing a compound represented by the formula (Ib) or (Ib') in accordance with the following reaction formula.

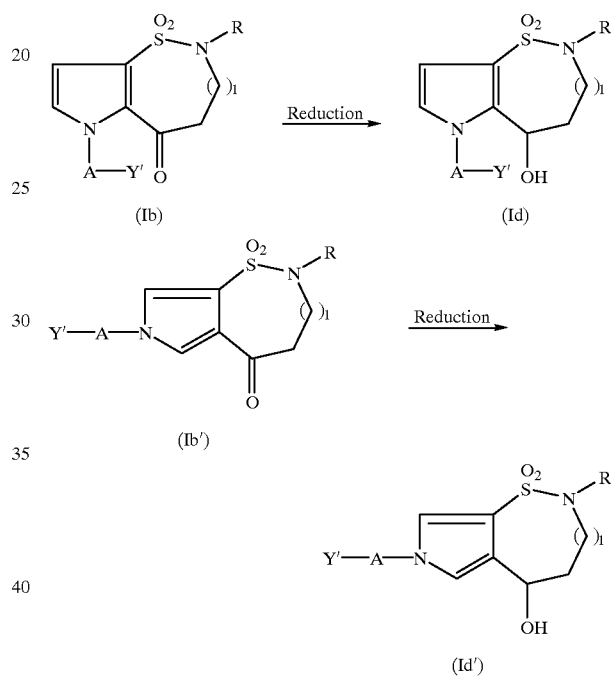

wherein A, R, Y' and l have the same meanings as defined above.

The conversion from the compound (Ib) or (Ib') into the compound (Id) or (Id') can be effected under similar conditions as in the conversion from the compound (IV) into the compound (IX) shown above under Process (a) of Process 4.

Process 5

Among the pyrrolesulfonamide compounds (I), the compounds (Ig) and (Ig') in each of which the bond indicated by the dashed line is present and $Z_1$ represents a hydrogen atom can be synthesized by any one of the following processes.

Process (a)

Each compound (Ig) or (Ig') is obtained in accordance with the following reaction scheme, namely, by subjecting a compound represented by the formula (IX) or (IX') to a dehydration reaction to obtain a compound represented by the formula (X) or (X') and then causing a nitrogen-containing compound (V) to act on the compound (X) or (X').

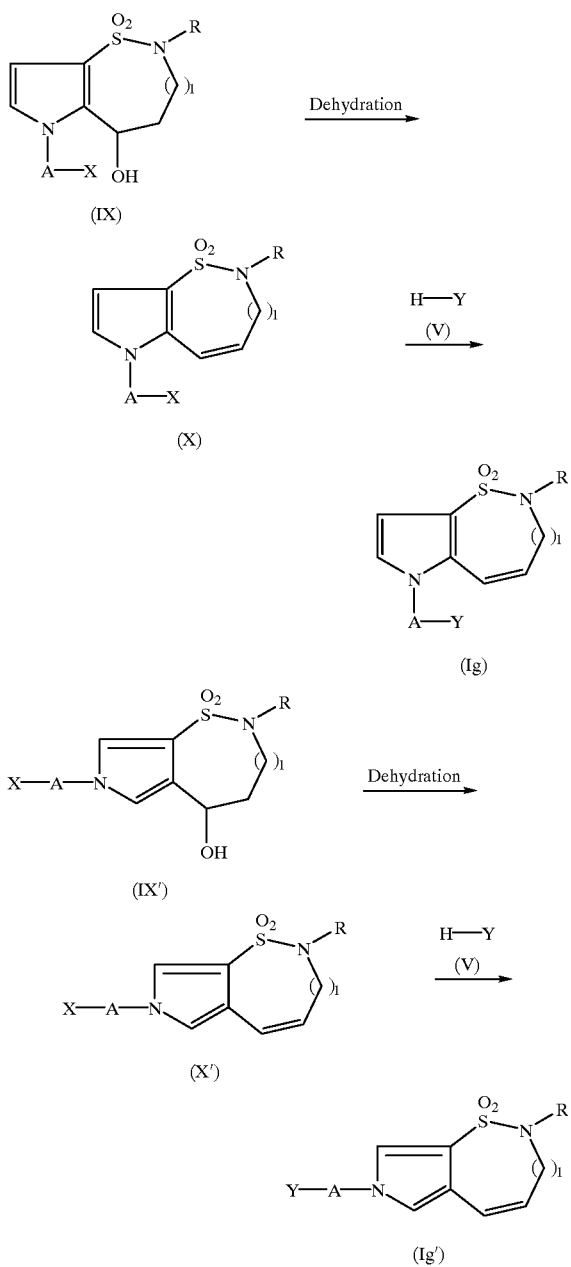

wherein A, R, X, Y and l have the same meanings as defined above.

In the above-described reaction, the conversion from the compound (IX) or (IX') into the compound (X) or (X') can be effected by treating the compound (IX) or (IX') with an acid such as hydrogen chloride, hydrogen bromide, sulfuric acid, methanesulfonic acid or p-toluenesulfonic acid at −20° C. to 100° C., preferably at −20° C. to room temperature in a solvent such as water, methanol, ethanol, ethyl acetate, chloroform or toluene.

As an alternative, the conversion into the compound (X) or (X') can also be effected by causing methanesulfonyl chloride, p-toluenesulfonyl chloride, phosphorus trichloride, phosphorus oxychloride, thionyl chloride or the like and a base such as triethylamine, pyridine or collidine to act on the compound (IX) or (IX') in a solvent such as dichloromethane, chloroform or toluene.

The conversion from the compound (X) or (X') into the compound (Ig) or (Ig') can be effected under similar conditions as in the conversion from the compound (IV) into the compound (Ia) described above under Process (a) of Process 2.

Process (b)

Each compound (Ig) or (Ig') is obtained by subjecting a compound represented by the formula (If) or (If') to a dehydration reaction in accordance with the following reaction formula:

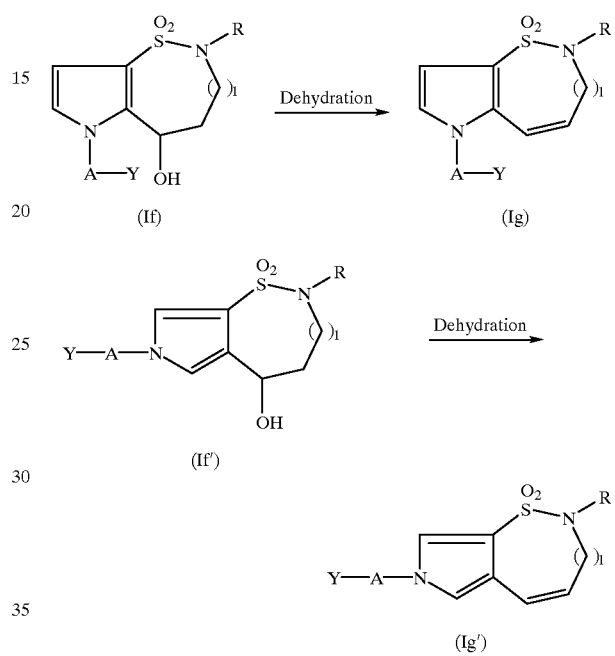

wherein A, R, Y and l have the same meanings as defined above.

In the above-described reaction, the conversion from the compound (If) or (If') into the compound (Ig) or (Ig') can be effected under similar conditions as in the conversion from the compound (IX) into the compound (X) described above under Process (a) of Process 5.

If necessary, the compounds (I) of the present invention obtained according to the above-described processes can each be reacted with one of various acids to convert the compound into its salt. Then, the resulting salt can be purified by a method such as recrystallization or column chromatography.

Exemplary acids usable for the conversion of the pyrrole-sulfonamide compounds (I) into their salts can include inorganic acids such as hydrochloric acid, nitric acid, sulfuric acid, phosphoric acid and hydrobromic acid; and organic acids such as maleic acid, fumaric acid, tartaric acid, lactic acid, citric acid, acetic acid, methanesulfonic acid, p-toluenesulfonic acid, adipic acid, palmitic acid and tannic acid.

Further, the compounds (I) according to the present invention include those containing asymmetric centers. Each racemic mixture can be isolated by one or more of various methods, whereby a single optically-active substance can be obtained. Usable methods include, for example:

(1) Isolation by an optically active column.
(2) Isolation by recrystallization subsequent to conversion into a salt with an optically active acid.

(3) Isolation by an enzyme reaction.
(4) Isolation by a combination of the above methods (1) to (3).

The pyrrolesulfonamide compounds (I) and their salts, which are obtained as described above, have strong serotonin-2 blocking action as will be demonstrated in tests to be described subsequently herein. Moreover, the compounds (I) according to the present invention have also been found to include those also having $\alpha_1$-blocking action. From the results of toxicity tests, the compounds (I) and salt thereof according to the present invention have also been found to possess high safety. The compounds and salt thereof according to the present invention can therefore be used as pharmaceuticals for the treatment of circulatory diseases such as ischemic heart diseases, cerebrovascular disturbances, peripheral circulatory disturbances and hypertension.

When the pyrrolesulfonamide compounds (I) according to this invention are used as pharmaceuticals, they can be administered in an effective dose as they are. As an alternative, they can also be formulated into various preparation forms by known methods and then administered.

Exemplary preparation forms as medicines include orally administrable preparation forms such as tablets, capsules and syrups as well as parenterally administrable preparation forms such as injections and suppositories. Whichever preparation form is used, a known liquid or solid extender or carrier usable for the formulation of the preparation form can be employed.

Examples of such extender or carrier include polyvinylpyrrolidone, arabic gum, gelatin, sorbit, cyclodextrin, tragacanth gum, magnesium stearate, talc, polyethylene glycol, polyvinyl alcohol, silica, lactose, crystalline cellulose, sugar, starch, calcium phosphate, vegetable oil, carboxymethylcellulose, sodium laurylsulfate, water, ethanol, glycerin, mannitol, syrup, and the like.

When the compounds (I) according to the present invention are used as pharmaceuticals, their dose varies depending on the administration purpose, the age, body weight, conditions, etc. of the patient to be administered. In oral administration, the daily dose may generally be about 0.01–1,000 mg.

The present invention will next be described in further detail by the following examples and tests. It is however to be noted that the present invention is by no means limited to the following examples.

EXAMPLE 1

Synthesis of sodium 3-pyrrolesulfonate (Compound 1)

A mixture consisting of 30.0 g (447 mmol) of pyrrole, 75.0 g (471 mmol) of sulfur trioxide.pyridine complex and 250 ml of 1,2-dichloroethane was refluxed for 16 hours. The top layer of the reaction mixture was removed by decantation. To the residue, 150 ml of water and 30 g of sodium carbonate were added successively. After the resulting mixture was boiled, the solvent was distilled off under reduced pressure. Ethanol-water (9:1 v/v, 500 ml) was added to the residue, followed by reflux for 1 hour. The reaction mixture was subjected to hot filtration, and the filtrate was allowed to cool down. Precipitated crystals were collected, washed with chilled ethanol and diethyl ether, and then dried under reduced pressure, whereby 17.0 g of powdery crystals were obtained.

EXAMPLE 2

Synthesis of benzyl 2-(3-pyrrolesulfonamide)acetate (Compound 2)

A suspension of 16.9 g (100 mmol) of Compound 1 and 22.9 g (110 mmol) of phosphorus pentachloride in 750 ml of diethyl ether was stirred at room temperature for 2 hours, and was then refluxed for 4 hours. After the reaction mixture was allowed to cooled down, it was filtered. The filtrate was washed successively with ice water (twice), a chilled, saturated aqueous solution of sodium hydrogencarbonate, ice water and a chilled, saturated aqueous solution of sodium chloride. The organic layer was dried over anhydrous sodium sulfate and then concentrated under reduced pressure, whereby 11.2 g of 3-pyrrolesulfonyl chloride were obtained as crude crystals.

After a mixture consisting of the whole amount of the thus-obtained crude crystals, 32.6 g (96.6 mmol) of glycine benzyl ester p-toluenesulfonate, 19.6 g (193 mmol) of triethylamine and 250 ml of tetrahydrofuran (hereinafter called "THF") was refluxed for 6 hours, the reaction mixture was concentrated under reduced pressure. Ethyl acetate was added to the residue. The resulting mixture was washed successively with a 10% aqueous solution of citric acid, water and a saturated aqueous solution of sodium chloride, dried over anhydrous sodium sulfate, and then concentrated under reduced pressure. The residue was treated with activated carbon under heat in methanol and then recrystallized from methanol, whereby 12.6 g of the title compound were obtained (yield: 43%).

EXAMPLE 3

Synthesis of Benzyl 3-(3-pyrrolesulfonamide)-propionate (Compound 3)

A mixture consisting of 1.66 g (10 mmol) of 3-pyrrolesulfonyl chloride obtained by the process of Example 2, 7.03 g (20 mmol) of p-alanine benzyl ester p-toluenesulfonate, 4.05 g (40 mmol) of triethylamine and 100 ml of THF was refluxed for 16 hours. The reaction mixture was concentrated under reduced pressure, and ethyl acetate was added to the residue. The organic layer was washed successively with a saturated aqueous solution of sodium hydrogencarbonate, water, a 10% aqueous solution of citric acid, water and a saturated aqueous solution of sodium chloride, dried over anhydrous sodium sulfate, and then concentrated under reduced pressure. The residue was purified by column chromatography on silica gel (Merck & Co. Inc. No. 9385) (the same silica gel were used in the subsequent examples) (eluent: ethyl acetate/hexane=1/1), whereby 2.82 g of the title compound were obtained (yield: 92%).

EXAMPLE 4

Synthesis of ethyl 2-[N-methyl-(3-pyrrolesulfonamide)]acetate (Compound 4)

In 400 ml of THF, 19.87 g (120 mmol) of 3-pyrrolesulfonyl chloride obtained by the process of Example 2 and 27.65 g (180 mmol) of sarcosine ethyl ester hydrochloride were suspended. A solution of 36.43 g (360 mmol) of triethylamine in 100 ml of THF was added under stirring, followed by refluxing for 16 hours. The reaction mixture was filtered, the filtrate was concentrated under reduced pressure, and ethyl acetate was then added to the residue. The organic layer was washed successively with a 10% aqueous solution of citric acid, water, a saturated aqueous solution of sodium hydrogencarbonate, water and a saturated aqueous solution of sodium chloride. The resulting organic solution was dried over anhydrous sodium sulfate and was then concentrated under reduced pressure. The residue was recrystallized from ethyl acetate-isopropyl ether, whereby 18.49 g of the title compound were obtained (yield: 63%).

EXAMPLE 5

Synthesis of ethyl 3-[N-methyl-(3-pyrrolesulfonamide)]propionate (Compound 5)

To a solution of 994 mg (6 mmol) of 3-pyrrolesulfonyl chloride, which had been obtained by the process of Example 2, in 40 ml of THF, a solution of 1.18 g (9 mmol) of ethyl 3-methylaminopropionate and 911 mg (9 mmol) of triethylamine in 10 ml of THF was slowly added under ice-cooled stirring, followed by refluxing for 16 hours. Post-treatment was conducted in a similar manner as in Example 4, and the residue was purified by chromatography on a silica gel column (eluent: ethyl acetate/hexane=1/1), whereby 1.24 g of the title compound were obtained (yield: 80%).

EXAMPLE 6

Synthesis of 2-(3-pyrrolesulfonamide)acetic acid (Compound 6)

To a solution of 4.85 g (16 mmol) of Compound 2 in 150 ml of THF, 480 mg of 10% palladium on charcoal were added, followed by stirring at room temperature for 15 hours under a hydrogen gas stream. The reaction mixture was filtered and the filtrate was concentrated under reduced pressure. The residue was recrystallized from acetonitrile, whereby 2.87 g of the title compound were obtained (yield: 88%).

EXAMPLE 7

Synthesis of 3-(3-pyrrolesulfonamide)propionic acid (Compound 7)

To a solution of 19.60 g (64 mmol) of Compound 3 in 400 ml of THF, 1.96 g of 5% palladium on charcoal were added, followed by stirring at room temperature for 4 hours under a hydrogen gas stream. The reaction mixture was filtered and the filtrate was concentrated under reduced pressure. The residue was recrystallized from ethyl acetate, whereby 11.96 g of the title compound were obtained (yield: 86%).

EXAMPLE 8

Synthesis of 2-[N-methyl-(3-pyrrolesulfonamide)]-acetic acid (Compound 8)

A mixture consisting of 4.93 g (20 mmol) of Compound 4 and 60 ml of a 1 N aqueous solution of sodium hydroxide was stirred at 50° C. for 30 minutes and then at room temperature for 1 hour. 6 N hydrochloric acid was added to the reaction mixture to acidify the same. The resulting mixture was ice-cooled. Precipitated crystals were collected by filtration, washed with water, and then dried. The filtrate was concentrated under reduced pressure, and ethyl acetate was added to the residue. The organic layer was washed with a saturated aqueous solution of sodium chloride, dried over anhydrous sodium sulfate, and then concentrated under reduced pressure. The residue and the above-obtained crystals were combined together and then recrystallized from ethyl acetate-hexane, whereby 4.11 g of the title compound were obtained (yield: 94%).

EXAMPLE 9

Synthesis of 3-[N-methyl-(3-pyrrolesulfonamide)]-propionic acid (Compound 9)

A mixture consisting of 16.46 g (63 mmol) of Compound 5 and 253 ml of a 1 N aqueous solution of sodium hydroxide was stirred at 60° C. for 6 hours. 6 N hydrochloric acid was added to the reaction mixture to acidify the same. Subsequent to saturation with sodium chloride, the resulting mixture was extracted with ethyl acetate (3 times). The organic layer was washed with a saturated aqueous solution of sodium chloride, dried over anhydrous sodium sulfate, and then concentrated under reduced pressure. The residue was recrystallized from ethyl acetate-benzene, whereby 13.05 g of the title compound were obtained (yield: 89%).

EXAMPLE 10

Synthesis of 2,3,4,5-tetrahydropyrrolo[2,3-e][1,2]-thiazin-4-one 1,1-dioxide (Compound 10) and 2,3,4,6-tetrahydropyrrolo[3,4-e][1,2]thiazin-4-one 1,1-dioxide (Compound 11)

Under ice cooling, 5.00 g (24.5 mmol) of Compound 6, 4.27 ml (49 mmol) of oxalyl chloride, 120 ml of THF and 3 droplets of DMF were mixed, and the resulting mixture was stirred for 1 hour. The reaction mixture was concentrated under reduced pressure. To the residue, 120 ml of 1,2-dichloroethane were added, followed by the addition of 6.53 g (49 mmol) of aluminum chloride under ice-cooled stirring. The thus-obtained mixture was stirred at the same temperature for 2.5 hours. Under ice-cooling, 43 ml of 6 N hydrochloric acid were added. Subsequent to saturation with sodium chloride, the resulting mixture was extracted with THF (3 times). The organic layer was washed with a saturated aqueous solution of sodium chloride, dried over anhydrous sodium sulfate, and then concentrated under reduced pressure. The residue was separated by chromatography on a silica gel column (eluent: ethyl acetate/hexane= 1/1→2/1), whereby 2.27 g of Compound 10 and 62 mg of Compound 11 were obtained (yields: 50% and 1%, respectively).

EXAMPLE 11

Synthesis of 2-methyl-2,3,4,5-tetrahydropyrrolo[2,3-e][1,2]thiazin-4-one 1,1-dioxide (Compound 12)

A mixture consisting of 436 mg (2 mmol) of Compound 8 and 24 g of polyphosphoric acid was stirred for 30 minutes over an oil bath of 80° C. The reaction mixture was ice-cooled, followed by the addition of about 30 ml of ice water. A 4 N aqueous solution of sodium hydroxide was added to adjust the pH to 5. Subsequent to saturation with sodium chloride, the resulting mixture was extracted with THF (3 times). The organic layer was washed with a saturated aqueous solution of sodium chloride, dried over anhydrous sodium sulfate, and then concentrated under reduced pressure. The residue was purified by chromatography on a silica gel column (eluent: ethyl acetate/hexane= 1/1), whereby 134 mg of the title compound were obtained (yield: 33%).

EXAMPLE 12

Synthesis of 3,4,5,6-tetrahydro-2H-pyrrolo[2,3-f]-[1,2]thiazepin-5-one 1,1-dioxide (Compound 13) and 3,4,5,7-tetrahydro-2H-pyrrolo[3,4-f][1,2]thiazepin-5-one 1,1-dioxide (Compound 14)

Under ice cooling, 436 mg (2 mmol) of Compound 7, 1 ml (11 mmol) of oxalyl chloride, 40 ml of THF and 1 droplet of DMF were mixed, and the resulting mixture was stirred at room temperature for 20 hours. The reaction mixture was concentrated under reduced pressure. To the residue, 50 ml of 1,2-dichloroethane were added, followed by the addition of 533 mg (4 mmol) of aluminum chloride under ice-cooled stirring. The thus-obtained mixture was stirred at room temperature for 3 hours. The reaction mixture was poured into water, followed by the extraction with ethyl acetate (twice). The organic layer was washed with a saturated aqueous solution of sodium chloride, dried over anhydrous sodium sulfate, and then concentrated under reduced pressure. The residue was separated by chromatography on a silica gel column (eluent: methanol/chloroform=1/19), whereby 73 mg of Compound 13 and 59 mg of Compound 14 were obtained (yields: 18% and 14%, respectively).

EXAMPLE 13

Synthesis of 3,4,5,6-tetrahydro-2H-pyrrolo[2,3-f]-[1,2]thiazepin-5-one 1,1-dioxide (Compound 13) and 3,4,5,7-tetrahydro-2H-pyrrolo[3,4-f][1,2]thiazepin-5-one 1,1-dioxide (Compound 14)— (Alternative Process)

A mixture consisting of 6.00 g (27.5 mmol) of Compound 7 and 300 g of polyphosphoric acid was stirred for 1 hour over an oil bath of 100° C. The reaction mixture was ice-cooled and then poured into ice water. A concentrated aqueous solution of sodium hydroxide was added to adjust the pH to 4. Post-treatment was conducted in a similar manner as in Example 11. The residue was separated by chromatography on a silica gel column (eluent: ethyl acetate/hexane=2/1), whereby 2.50 g of Compound 13 and 497 mg of Compound 14 were obtained (yields: 46% and 9%, respectively).

EXAMPLE 14

Synthesis of 2-methyl-3,4,5,6-tetrahydro-2H-pyrrolo[2,3-f][1,2]thiazepin-5-one 1,1-dioxide (Compound 15) and 2-methyl-3,4,5,7-tetrahydro-2H-pyrrolo[3,4-f][1,2]thiazepin-5-one 1,1-dioxide (Compound 16)

A mixture consisting of 500 mg (2.15 mmol) of Compound 9 and 25 g of polyphosphoric acid was stirred for 1 hour over an oil bath of 80° C. The reaction mixture was ice-cooled and then poured into ice water. Subsequent to saturation with sodium chloride, the resulting mixture was extracted with THF (3 times). The organic layer was washed with a saturated aqueous solution of sodium chloride, dried over anhydrous sodium sulfate, and then concentrated under reduced pressure. The residue was separated by column chromatography on alumina (Merck & Co. Inc. No. 1097) (eluent: ethyl acetate) and further by chromatography on a silica gel column (eluent: ethyl acetate/hexane=1/1), whereby 175 mg of Compound 15 and 36 mg of Compound 16 were obtained (yields: 38% and 8%, respectively).

EXAMPLE 15

Synthesis of 5-(4-chlorobutyl)-2-methyl-2,3,4,5-tetrahydropyrrolo[2,3-e][1,2]thiazin-4-one 1,1-dioxide (Compound 17)

A suspension of 400 mg (2 mmol) of Compound 12, 1.37 g (8 mmol) of 1-bromo-4-chlorobutane and 1.11 g (8 mmol) of potassium carbonate in 20 ml of 2-butanone was refluxed for 3 hours. The reaction mixture was filtered, and the filtrate was concentrated under reduced pressure. The residue was purified by chromatography on a silica gel column (eluent: ethyl acetate/hexane=1/2), whereby 582 mg of the title compound were obtained (yield: 100%).

EXAMPLE 16

Synthesis of 6-(4-chlorobutyl)-2-methyl-3,4,5,6-tetrahydro-2H-pyrrolo[2,3-f][1,2]thiazepin-5-one 1,1-dioxide (Compound 18)

A suspension of 429 mg (2 mmol) of Compound 15, 1.37 g (8 mmol) of 1-bromo-4-chlorobutane and 1.11 g (8 mmol) of potassium carbonate in 30 ml of 2-butanone was refluxed for 20 hours. The reaction mixture was concentrated under reduced pressure. A 10% aqueous solution of citric acid was added to the residue, and the thus-obtained mixture was extracted with chloroform (3 times). The organic layer was washed successively with water and a saturated aqueous solution of sodium chloride, dried over anhydrous sodium sulfate, and then concentrated under reduced pressure. The residue was purified by chromatography on a silica gel column (eluent: ethyl acetate/hexane=1/2), whereby 535 mg of the title compound were obtained (yield: 88%).

EXAMPLE 17

Synthesis of 7-(4-chlorobutyl)-2-methyl-3,4,5,7-tetrahydro-2H-pyrrolo[3,4-f][1,2]thiazepin-5-one 1,1-dioxide (Compound 19)

A suspension of 257 mg (1.2 mmol) of Compound 16, 823 mg (4.8 mmol) of 1-bromo-4-chlorobutane and 663 mg (4.8 mmol) of potassium carbonate in 30 ml of 2-butanone was refluxed for 20 hours. Post-treatment was conducted in a similar manner as in Example 16. The residue was purified by chromatography on a silica gel column (eluent: ethyl acetate/hexane=1/1), whereby 306 mg of the title compound were obtained (yield: 84%).

EXAMPLE 18

Synthesis of 5-(4-chlorobutyl)-4-hydroxyimino-2-methyl-2,3,4,5-tetrahydropyrrolo[2,3-e][1,2]thiazine 1,1-dioxide (Compound 20)

A suspension of 145 mg (0.5 mmol) of Compound 17, 104 mg (1.5 mmol) of hydroxylamine hydrochloride and 123 mg (1.5 mmol) of sodium acetate in 15 ml of methanol was refluxed for 166 hours. The reaction mixture was concentrated under reduced pressure, followed by the addition of a half-saturated aqueous solution of potassium carbonate to the residue. The resulting mixture was extracted with chloroform (twice). The organic layer was washed with a saturated aqueous solution of sodium chloride, dried over anhydrous sodium sulfate, and then concentrated under reduced pressure. The residue was purified by chromatography on a silica gel column (eluent: chloroform), whereby 69 mg of the title compound were obtained (yield: 45%).

EXAMPLE 19

Synthesis of 6-(4-chlorobutyl)-5-hydroxyimino-2-methyl-3,4,5,6-tetrahydro-2H-pyrrolo[2,3-f][1,2]-thiazepine 1,1-dioxide (Compound 21)

A suspension of 152 mg (0.5 mmol) of Compound 18, 174 mg (2.5 mmol) of hydroxylamine hydrochloride and 205 mg (2.5 mmol) of sodium acetate in 20 ml of ethanol was refluxed for 20 hours. The reaction mixture was concentrated under reduced pressure, followed by the addition of water to the residue. The resulting mixture was extracted with chloroform (3 times). The organic layer was washed with a saturated aqueous solution of sodium chloride, dried over anhydrous sodium sulfate, and then concentrated under reduced pressure. The residue was purified by chromatography on a silica gel column (eluent: methanol/chloroform=3/97), whereby 116 mg of the title compound were obtained (yield: 73%).

EXAMPLE 20

Synthesis of 5-[4-[4-(4-fluorobenzoyl)piperidino]-butyl]-2-methyl-2,3,4,5-tetrahydropyrrolo[2,3-e]-[1,2]thiazin-4-one 1,1-dioxide (Compound 22)

A suspension of 145 mg (0.5 mmol) of Compound 17, 134 mg (0.55 mmol) of 4-(4-fluorobenzoyl)piperidine hydrochloride, 185 mg (2.2 mmol) of sodium hydrogencarbonate and 165 mg (1.1 mmol) of sodium iodide in 20 me of acetonitrile was refluxed for 50 hours. Posttreatment was conducted in a similar manner as in Example 18. The residue was purified by chromatography on a silica gel column (eluent: methanol/chloroform=3/97), whereby 220 mg of the title compound were obtained (yield: 95%).

EXAMPLE 21

Synthesis of 5-[4-[4-(4-fluorophenyl)piperazin-1-yl]butyl]-2-methyl-2,3,4,5-tetrahydropyrrolo[2,3-e]-[1,2]thiazin-4-one 1,1-dioxide (Compound 23)

A suspension of 233 mg (0.8 mmol) of Compound 17, 216 mg (1.2 mmol) of 1-(4-fluorophenyl)piperazine, 166 mg (1.2 mmol) of potassium carbonate and 240 mg (1.6 mmol) of sodium iodide in 20 ml of acetonitrile was refluxed for 23 hours. Post-treatment was conducted in a similar manner as in Example 18. The residue was purified by chromatography on a silica gel column (eluent: methanol/chloroform=1/49), whereby 291 mg of the title compound were obtained (yield: 84%).

EXAMPLE 22

Synthesis of 7-[4-[4-(2-methoxyphenyl)piperazin-1-yl]butyl]-2-methyl-3,4,5,7-tetrahydro-2H-pyrrolo-[3,4-f][1,2]thiazepin-5-one 1,1-dioxide (Compound 24)

A suspension of 152 mg (0.5 mmol) of Compound 19, 144 mg (0.75 mmol) of 1-(2-methoxyphenyl)piperazine, 104 mg (0.75 mmol) of potassium carbonate and 150 mg (1 mmol) of sodium iodide in 20 ml of acetonitrile was refluxed for 17 hours. Post-treatment was conducted in a similar manner as in Example 18. The residue was purified by chromatography on a silica gel column (eluent: methanol/chloroform=1/19), whereby 160 mg of the title compound were obtained (yield: 99%).

EXAMPLE 23

Synthesis of 5-[3-[4-(4-fluorophenyl)piperazin-1-yl]propyl]-2-methyl-2,3,4,5-tetrahydropyrrolo[2,3-e][1,2]thiazin-4-one 1,1-dioxide (Compound 25)

A suspension of 200 mg (1 mmol) of Compound 12, 385 mg (1.5 mmol) of 1-(3-chloropropyl)-4-(4-fluorophenyl)piperazine and 207 mg (1.5 mmol) of potassium carbonate in 15 ml of 2-butanone was refluxed for 24 hours. The reaction mixture was filtered, and the filtrate was concentrated under reduced pressure. The residue was purified by chromatography on a silica gel column (eluent: chloroform), whereby 335 mg of the title compound were obtained (yield: 80%).

EXAMPLE 24

Synthesis of 6-[3-[4-(4-fluorophenyl)piperazin-1-yl]propyl]-2-methyl-3,4,5,6-tetrahydro-2H-pyrrolo-[2,3-f][1,2]thiazepine 1,1-dioxide (Compound 26)

A suspension of 214 mg (1 mmol) of Compound 15, 385 mg (1.5 mmol) of 1-(3-chloropropyl)-4-(4-fluorophenyl) piperazine and 207 mg (1.5 mmol) of potassium carbonate in 20 ml of 2-butanone was refluxed for 17 hours. Post-treatment was conducted in a similar manner as in Example 18. The residue was purified by chromatography on a silica gel column (eluent: ethyl acetate/hexane=4/1), whereby 400 mg of the title compound were obtained (yield: 92%).

EXAMPLE 25

Synthesis of 6-[3-[4-(4-fluorophenyl)piperazin-1-yl]propyl]-3,4,5,6-tetrahydro-2H-pyrrolo[2,3-f]-[1,2]thiazepin-5-one 1,1-dioxide (Compound 27)

A suspension of 200 mg (1 mmol) of Compound 13, 257 mg (1 mmol) of 1-(3-chloropropyl)-4-(4-fluorophenyl)piperazine and 138 mg (1 mmol) of potassium carbonate in 20 ml of dioxane was refluxed for 16 hours. The reaction mixture was filtered, and the filtrate was concentrated under reduced pressure. The residue was purified by chromatography on a silica gel column (eluent: methanol/chloroform=3/37), whereby 116 mg of the title compound were obtained (yield: 28%).

EXAMPLE 26

Synthesis of 5-[4-[4-(4-fluorobenzoyl)piperidino]-butyl]-4-hydroxyimino-2-methyl-2,3,4,5-tetrahydropyrrolo[2,3-e][1,2]thiazine 1,1-dioxide (Compound 28)

A suspension of 61 mg (0.2 mmol) of Compound 20, 54 mg (0.22 mmol) of 4-(4-fluorobenzoyl)piperidine hydrochloride, 74 mg (0.88 mmol) of sodium hydrogencarbonate and 66 mg (0.44 mmol) of sodium iodide in 10 ml of acetonitrile was refluxed for 29 hours. Posttreatment and purification were conducted in a similar manner as in Example 20, whereby 75 mg of the title compound were obtained (yield: 79%).

EXAMPLE 27

Synthesis of 6-[4-[4-(4-fluorobenzoyl)piperidino]-butyl]-5-hydroxyimino-2-methyl-3,4,5,6-tetrahydro-2H-pyrrolo[2,3-f][1,2]thiazepine 1,1-dioxide (Compound 29)

A suspension of 110 mg (0.34 mmol) of Compound 21, 83 mg (0.34 mmol) of 4-(4-fluorobenzoyl)piperidine hydrochloride, 114 mg (1.36 mmol) of sodium hydrogen-carbonate and 102 mg (0.68 mmol) of sodium iodide in 10 ml of acetonitrile was refluxed for 17 hours. Post-treatment was conducted in a similar manner as in Example 18. The residue was purified by chromatography on a silica gel column (eluent: methanol/chloroform=11/189), whereby 108 mg of the title compound were obtained (yield: 64%).

EXAMPLE 28

Synthesis of 5-[4-[4-(4-fluorophenyl)piperazin-1-yl]butyl]-4-hydroxyimino-2-methyl-2,3,4,5-tetrahydropyrrolo[2,3-e][1,2]thiazine 1,1-dioxide (Compound 30)

A suspension of 174 mg (0.4 mmol) of Compound 23 and 111 mg (1.6 mmol) of hydroxylamine hydrochloride in 10 ml of pyridine was stirred for 24 hours over an oil bath of 80° C. Post-treatment and purification were conducted in a similar manner as in Example 21, whereby 159 mg of the title compound were obtained (yield: 88%).

EXAMPLE 29

Synthesis of 5-[3-[4-(4-fluorophenyl)piperazin-1-yl] propyl]-4-hydroxyimino-2-methyl-2,3,4,5-tetrahydropyrrolo[2,3-e][1,2]thiazine 1,1-dioxide (Compound 31)

A suspension of 168 mg (0.4 mmol) of Compound 25 and 111 mg (1.6 mmol) of hydroxylamine hydrochloride in 10 ml of pyridine was stirred for 21 hours over an oil bath of 60° C. Post-treatment was conducted in a similar manner as in Example 18. The residue was purified by chromatography on a silica gel column (eluent: methanol/chloroform=1/99), whereby 144 mg of the title compound were obtained (yield: 83%).

EXAMPLE 30

Synthesis of 6-[3-[4-(4-fluorophenyl)piperazin-1-yl] propyl]-5-hydroxyimino-2-methyl-3,4,5,6-tetrahydro-2H-pyrrolo[2,3-f][1,2]thiazepine 1,1-dioxide (Compound 32)

A suspension of 174 mg (0.4 mmol) of Compound 26, 56 mg (0.8 mmol) of hydroxylamine hydrochloride and 66 mg (0.8 mmol) of sodium acetate in 20 ml of methanol was refluxed for 17 hours. Post-treatment and purification were conducted in a similar manner as in Example 20, whereby 119 mg of the title compound were obtained (yield: 66%).

Physical data of the compounds obtained in Examples 1–30 are shown in Tables 1–8.

TABLE 1

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 1 | 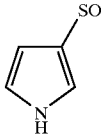 | Colorless powdery crystals ≧250° C. | (400MHz) (D$_2$O/TSP-d$_4$**) 6.44(1H, s), 6.89(1H, t, J=2.3Hz), 7.23(1H, s) | (KBr) 3588, 3287, 1539, 1487, 1186, 1078, 1055, 932, 750, 684, 654 |
| 2 | 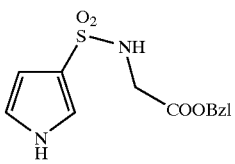 | Colorless needle crystals 132.0–134.0° C. (methanol) | (270MHz) (DMSO-d$_6$/TMS) 3.63(2H, d, J=6.6Hz), 5.08(2H, s), 6.29(1H, d, J=2.0Hz), 6.85(1H, m), 7.25(1H, d, J=2.0Hz), 7.30–7.41 (5H, m), 7.56(1H, t, J=6.6Hz), 11.49(1H, br.s) | (KBr) 3333, 3292, 1732, 1443, 1386, 1355, 1314, 1236, 1149, 1105, 1050, 863, 739 |
| 3 | 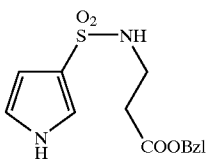 | Colorless powdery crystals 80.0–81.0° C. (ethyl acetate-hexane) | (270MHz) 2.60(2H, t, J=5.9Hz), 3.24(2H, m), 4.99(1H, m), 5.11(2H, s), 6.47(1H, m), 6.80(1H, q, J=2.64Hz), 7.27–7.42(6H, m), 8.68(1H, br.s) | (KBr) 3418, 3276, 1743, 1725, 1530, 1415, 1320, 1198, 1140, 1074, 996, 892, 804, 747, 680 |
| 4 | 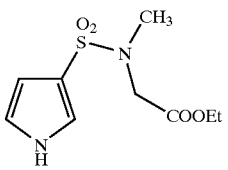 | Colorless prism crystals 79.0–81.0° C. (ethyl acetate-isopropyl ether) | (400MHz) 1.25(3H, t, J=7.1Hz), 2.86(3H, s), 3.89(2H, s), 4.16(2H, q, J=7.1Hz), 6.48(1H, m), 6.83(1H, m), 7.30(1H, m), 8.86(1H, br.s) | (KBr) 3325, 3127, 1733, 1528, 1337, 1231, 1149, 1026, 768 |

*Measured in CDCl$_3$ with TMS as an internal standard unless otherwise specifically indicated.
**TSP-d$_4$ = sodium 3-(trimethylsilyl)propionate-d$_4$

TABLE 2

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 5 | 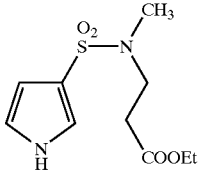 | Colorless oil | (400MHz) 1.26(3H, t, J=7.1Hz), 2.62(2H, t, J=7.2Hz), 2.75(3H, s), 3.28(2H, t, J=7.2Hz), 4.14(2H, q, J=7.1Hz), 6.45(1H, m), 6.84(1H, m), 7.26(1H, m), 9.09(1H, br.s) | (film) 3354, 1732, 1377, 1325, 1141, 1044, 961, 713 |

TABLE 2-continued

| Comp'd No. | Structural formula | Property m.p. (recryst'n solvent) | NMR (δ ppm)* ( ): observation frequency | IR (cm⁻¹) ( ): measuring method |
|---|---|---|---|---|
| 6 | (pyrrole-SO$_2$-NH-CH$_2$-COOH) | Pale yellow powdery crystals 151.5–152.5° C. (acetonitrile) | (270MHz) (DMSO-d$_6$/TMS) 3.46(2H, d, J=6.6Hz), 6.30(1H, dd, J=2.0Hz, 4.6Hz), 6.85(1H, dd, J=2.0Hz, 4.6Hz), 7.25(1H, m), 7.28(1H, t, J=6.6Hz), 11.48(1H, br.s), 12.58(1H, br.s) | (KBr) 3349, 3294, 1720, 1420, 1317, 1257, 1232, 1140, 1050, 843, 810, 743 |
| 7 | (pyrrole-SO$_2$-NH-CH$_2$CH$_2$-COOH) | Colorless powdery crystals 107.0–108.0° C. (ethyl acetate) | (270MHz) (DMSO-d$_6$/TMS) 2.35(2H, t, J=7.3Hz), 2.91(2H, m), 6.30(1H, m), 6.88(1H, m), 7.00(1H, m), 7.25(1H, m) 11.49(1H, br.s), 12.20(1H, br.s) | (KBr) 3324, 3264, 1724, 1537, 1490, 1407, 1368, 1303, 1269, 1231, 1186, 1147, 1128, 1085, 1060, 1046, 947, 927, 827, 726 |
| 8 | (pyrrole-SO$_2$-N(CH$_3$)-CH$_2$-COOH) | Colorless prism crystals 130.5–132.0° C. (ethyl acetate-hexane) | (400MHz) (DMSO-d$_6$/TMS) 2.66(3H, s), 3.66(2H, s), 6.34(1H, m), 6.92(1H, m), 7.34(1H, m), 11.64(1H, br.), 12.70(1H, br.s) | (KBr) 3363, 1720, 1529, 1452, 1408, 1333, 1250, 1228, 1149, 1089, 1044, 1021, 939, 898, 771 |

*Measured in CDCl$_3$ with TMS as an internal standard unless otherwise specifically indicated.

TABLE 3

| Comp'd No. | Structural formula | Property m.p. (recryst'n solvent) | NMR (δ ppm)* ( ): observation frequency | IR (cm⁻¹) ( ): measuring method |
|---|---|---|---|---|
| 9 | (pyrrole-SO$_2$-N(CH$_3$)-CH$_2$CH$_2$-COOH) | Colorless prism crystals 105.0–107.0° C. (ethyl acetate-benzene) | (270MHz) (DMSO-d$_6$/TMS) 2.47(2H, t, J=7.3Hz), 2.59(3H, s), 3.06(2H, t, J=7.3Hz), 6.32(1H, m), 6.93(1H, m), 7.32(1H, m), 11.69(1H, br.s), 12.29(1H, br.s) | (KBr) 3401, 1706, 1523, 1318, 1256, 1230, 1147, 1126, 1049, 953, 754 |
| 10 | (bicyclic pyrrole-fused sultam with ketone) | Colorless powdery crystals 204° C. (decomp'd) (acetonitrile) | (270MHz) (DMSO-d$_6$/TMS) 3.98(2H, d, J=7.3Hz), 6.59(1H, t, J=2.0Hz), 7.32(1H, t, J=2.0Hz), 8.22(1H, t, J=7.3Hz), 12.86(1H, br.) | (KBr) 3250, 1671, 1439, 1393, 1315, 1240, 1177, 1146, 1107, 761 |
| 11 | (bicyclic pyrrole-fused sultam with ketone, isomer) | Colorless powdery crystals 226.0–229.0° C. (acetonitrile) | (400MHz) (DMSO-d$_6$/TMS) 3.90(2H, s), 7.50(1H, d, J=1.9Hz), 7.58(1H, d, J=1.6Hz), 8.12(1H, br.s), 12.42(1H, br.s) | (KBr) 3282, 1660, 1543, 1515, 1419, 1364, 1323, 1232, 1178, 1158, 1139, 1082, 1064, 985, 843, 804, 777, 712 |
| 12 | (N-methyl bicyclic pyrrole-fused sultam with ketone) | Pale yellow prism crystals 169.0–175.5° C. (ethyl acetate-hexane) | (400MHz) 2.95(3H, s), 4.21(2H, s), 6.65(1H, d, J=2.5Hz), 7.18(1H, s), 9.83(1H, br.s) | (KBr) 3248, 3131, 1666, 1464, 1390, 1343, 1296, 1236, 1182, 1147, 1118, 1092, 1006, 920, 780, 710, 674 |

*Measured in CDCl$_3$ with TMS as an internal standard unless otherwise specifically indicated.

TABLE 4

| Comp'd No. | Structural formula | Property m.p. (recryst'n solvent) | NMR (δ ppm)* ( ): observation frequency | IR (cm⁻¹) ( ): measuring method |
| --- | --- | --- | --- | --- |
| 13 | (pyrrole fused thiazepinone structure) | Colorless prism crystals 184.0–186.0° C. (acetonitrile) | (400MHz) (DMSO-$d_6$/TMS) 2.89(2H, t, J=5.8Hz), 3.49(2H, m), 6.56(1H, d, J=2.7Hz), 7.17(1H, d, J=2.7Hz), 7.86(1H, br.), 12.33(1H, br.s) | (KBr) 3350–3000, 1610, 1440, 1381, 1318, 1227, 1144, 875, 775, 696 |
| 14 | (pyrrole fused thiazepinone structure) | Pale brown powdery crystals 183.0–187.0° C. (acetonitrile-isopropyl ether) | (400MHz) (DMSO-$d_6$/TMS) 2.85(2H, m), 3.40(2H, m), 7.40(1H, d, J=2.1Hz), 7.44(1H, d, J=2.1Hz), 7.71(1H, br.), 12.08(1H, br.s) | (KBr) 3263, 1621, 1512, 1419, 1344, 1303, 1270, 1131, 1080, 696 |
| 15 | (N-methyl pyrrole fused thiazepinone structure) | Colorless prism crystals 195.0–197.0° C. (acetonitrile-isopropyl ether) | (270MHz) (DMSO-$d_6$/TMS) 2.84(3H, s), 2.98(2H, m), 3.73(2H, m), 6.57(1H, d, J=2.6Hz), 7.20(1H, d, J=2.6Hz), 12.51(1H, br.s) | (KBr) 3283, 1630, 1531, 1384, 1322, 1220, 1143, 1016, 960, 863, 765, 732 |
| 16 | (N-methyl pyrrole fused thiazepinone structure) | Colorless needle crystals 132.0–136.0° C. (ethyl acetate-hexane) | (270MHz) (DMSO-$d_6$/TMS) 2.77(3H, s), 2.87(2H, m), 3.64(2H, m), 7.43–7.49(2H, m), 12.20(1H, br.s) | (KBr) 3330, 1638, 1500, 1322, 1225, 1120, 868, 788, 731 |

*Measured in CDCl₃ with TMS as an internal standard unless otherwise specifically indicated.

TABLE 5

| Comp'd No. | Structural formula | Property m.p. (recryst'n solvent) | NMR (δ ppm)* ( ): observation frequency | IR (cm⁻¹) ( ): measuring method |
| --- | --- | --- | --- | --- |
| 17 | (N-methyl, N-(CH₂)₄Cl pyrrole fused thiazinone structure) | Yellow oil | (400MHz) 1.79(2H, m), 1.95(2H, m), 2.93(3H, s), 3.56(2H, t, J=6.3Hz), 4.16(2H, s), 4.38(2H, t, J=7.2Hz), 6.56(1H, d, J=2.7Hz), 7.02(1H, d, J=2.7Hz) | (film) 3131, 2960, 1671, 1508, 1475, 1393, 1341, 1205, 1160, 1111, 1061, 1001, 918, 721, 650 |
| 18 | (N-methyl, N-(CH₂)₄Cl pyrrole fused thiazepinone structure) | Colorless oil | (400MHz) 1.78(2H, m), 1.91(2H, m), 2.80(3H, s), 3.22(2H, m), 3.47–3.58(4H, m), 4.32(2H, t, J=7.2Hz), 6.67(1H, d, J=2.8Hz), 6.89(1H, d, J=2.8Hz) | (film) 1658, 1470, 1395, 1332, 1190, 1153, 720 |

TABLE 5-continued

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 19 | (structure with Cl(CH$_2$)$_4$-N, pyrrole fused to ring with O$_2$S-N-CH$_3$, ketone O) | Colorless prism crystals 123.5–125.5° C. (ethyl acetate-isopropyl ether) | (400MHz) 1.78(2H, m), 2.01(2H, m), 2.87(3H, s), 3.02(2H, m), 3.55(2H, t, J=6.3Hz), 3.69(2H, m), 3.96(2H, t, J=7.1Hz), 7.21(1H, d, J=2.5Hz), 7.31(1H, d, J=2.5Hz) | (KBr) 1651, 1526, 1330, 1152, 1033, 870, 840, 735, 705 |
| 20 | (structure with (CH$_2$)$_4$Cl-N, pyrrole fused to ring with O$_2$S-N-CH$_3$, =NOH) | Colorless prism crystals 107.5–108.5° C. (ethyl acetate-hexane) | (400MHz) 1.77(2H, m), 1.92(2H, m), 2.78(3H, s), 3.54(2H, t, J=6.4Hz), 4.25(2H, t, J=7.2Hz), 4.59(2H, s), 6.52(1H, d, J=2.9Hz), 6.77(1H, d, J=2.9Hz), 7.45(1H, s) | (KBr) 3348, 1479, 1456, 1409, 1326, 1314, 1204, 1158, 1112, 1079, 986, 934 753, 700 |

*Measured in CDCl$_3$ with TMS as an internal standard unless otherwise specifically indicated.

TABLE 6

| Comp'd No. | Structural formula | Property m.p. (recryst'n solvent) | NMR (δ ppm)* ( ): observation frequency | IR (cm⁻¹) ( ): measuring method |
|---|---|---|---|---|
| 21 | (structure: methylsulfonyl-N-methyl pyrrole fused ring with =NOH and N(CH₂)₄Cl) | Colorless oil | (400MHz) 1.73(2H, m), 1.89(2H, m), 2.81(3H, s), 3.09(2H, m), 3.51(2H, t, J=6.4Hz), 3.62(2H, m), 4.10(2H, t, J=7.2Hz), 6.58(1H, d, J=3.0Hz), 6.66(1H, d, J=3.0Hz), 8.08(1H, s) | (film) 3405, 2958, 1324, 1192, 1146, 967, 736 |
| 22 | (structure with 4-fluorobenzoyl piperidine) | Yellow oil … [monohydrochloride] Pale yellow powdery crystals 203.0–206.5° C. (ethanol-ether) | (400MHz) 1.53(2H, m), 1.76–1.92(6H,m), 2.12(2H, m), 2.39(2H, t, J=7.2Hz), 2.92(3H, s), 2.95(2H, m), 3.20(1H, m), 4.13(2H, s), 4.36(2H, t, J=7.3Hz), 6.53(1H, d, J=2.7Hz), 7.00(1H, d, J=2.7Hz), 7.13(2H, m), 7.95(2H, m) | (film) 2945, 1674, 1597, 1506, 1475, 1392, 1343, 1206, 1158, 1001, 918, 854, 736 |
| 23 | (structure with 4-fluorophenyl piperazine) | Pale yellow prism crystals 92.0–93.5° C. (ethyl acetate-hexane) | (400MHz) 1.54(2H, m), 1.83(2H, m), 2.40(2H, t, J=7.3Hz), 2.57(4H, m), 2.92(3H, s), 3.10(4H, m), 4.14(2H, s), 4.37(2H, t, J=7.3Hz), 6.54(1H, d, J=2.7Hz), 6.86(2H, m), 6.95(2H, m), 7.00(1H, d, J=2.7Hz), 7.20(2H, m) | (KBr) 2821, 1668, 1509, 1475, 1394, 1340, 1233, 1156, 1002, 918, 830, 739, 712, 664 |
| 24 | (structure with 2-methoxyphenyl piperazine) | Colorless powdery crystals 122.5–123.5° C. (ethyl acetate-isopropyl ether) | (400 MHz) 1.53(2H, m), 1.88(2H, m), 2.42(2H, t, J=7.2Hz), 2.57–2.66(4H, m), 2.86 (3H, s), 3.01(2H, m), 3.04–3.13 (4H, m), 3.68(3H, m), 3.86(3H, s), 3.94(2H, t, J=7.2 Hz), 6.83–7.03 (4H, m), 7.20 (1H, d, J=2.5Hz), 7.32 (1H, d, J=2.5Hz) | (KBr) 2819, 1663, 1526, 1498, 1322, 1237, 1150, 1028, 755, 719 |

*Measured in CDCl₃ with TMS as an internal standard unless otherwise specifically indicated.

TABLE 7

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 25 | | Pale brown prism crystals 97.0–98.5° C. (ethyl acetate-hexane) | (400MHz) 1.97(2H, quint., J=6.8Hz), 2.35(2H, t, J=6.7Hz), 2.57(4H, m), 2.93(3H, s), 3.13(4H, m), 4.14(2H, s), 4.42(2H, t, J=6.9Hz), 6.53(1H, d, J=2.7Hz), 6.87(2H, m), 6.96(2H, m), 7.05(1H, d, J=2.7Hz) | (KBr) 2824, 1672, 1508, 1476, 1390, 1339, 1230, 1208, 1155, 1002, 961, 914 823, 766, 737, 680 |
| 26 | | Yellow oil | (270MHz) 1.96(2H, quint., J=7.0Hz), 2.35(2H, t, J=7.0Hz), 2.52–2.62 (4H, m), 2.80(3H, s), 3.07–3.17(4H, m), 3.23(2H, m), 3.52(2H, m), 4.37(2H, t, J=7.0Hz), 6.66(1H, d, J=2.6Hz), 6.83–7.02 (5H, m) | (film) 2820, 1658, 1510, 1333, 1233, 1151, 719 |
| 27 | | COlorless powdery crystals 134.5–135.5° C. (ethyl acetate-isopropyl ether) | (270MHz) 1.94(2H, m), 2.35(2H, t, J=7.0Hz), 2.44–2.68(4H, m), 3.01–3.20(4H, m), 3.27(2H, m), 3.50(2H, m), 4.34(2H, t, J=6.6Hz), 5.09(1H, m), 6.66(1H, d, J=2.6Hz), 6.81–7.05 (5H, m) | (KBr) 2830, 1667, 1509, 1400, 1327, 1210, 1148, 1104, 955 |
| 28 | | Colorless powdery crystals 189.5–191.0° C. (ethyl acetate-hexane) | (400MHz) 1.59 (2H, m), 1.80(2H, quint., J=7.4Hz), 1.84–1.97(4H, m), 2.20(2H, m), 2.43(2H, t, J=7.4Hz), 2.78(3H, s), 3.00 (2H, m), 3.26(1H, m), 4.26(2H, t, J=7.4Hz), 4.59(2H, s), 6.50(1H, d, J=3.0Hz), 6.75(1H, d, J=3.0Hz), 7.14 (2H, m), 7.96(2H, m), 10.42(1H, br.s) | (KBr) 2953, 1676, 1598, 1508, 1451, 1328, 1227, 1208, 1153, 976, 946, 856, 744, 675 |

*Measured in CDCl$_3$ with TMS as an internal standard unless otherwise specifically indictaed.

TABLE 8

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 29 | (structure with pyrrole fused to S(O$_2$)-N(CH$_3$) seven-membered ring, =NOH, (CH$_2$)$_4$N-piperidine-C(O)-C$_6$H$_4$-F) | Colorless powdery crystals 184.0–185.5° C. (decomp'd) (2-butanone) | (400MHz) 1.57(2H, m), 1.79(2H, m), 1.85–1.92 (4H, m), 2.08–2.24 (2H, m), 2.40(2H, t, J=7.3Hz), 2.81 (3H, s), 2.94–3.04(2H, m), 3.10(2H, m), 3.25(1H, m), 3.63(2H, m), 4.10(2H, t, J=7.3Hz), 6.58(1H, d, J=2.9Hz), 6.65(1H, d, J=2.9Hz), 7.14 (2H, t, J=8.6Hz), 7.96 (2H, m), 10.20 (1H, br.) | (KBr) 2968, 1683, 1596, 1333, 1204, 1147, 994, 970, 738 |
| 30 | (structure with pyrrole fused to S(O$_2$)-N(CH$_3$) six-membered ring, =NOH, (CH$_2$)$_4$N-piperazine-C$_6$H$_4$-F) | Colorless needle crystals 178.0–180.0° C. (ethyl acetate-hexane) | (400MHz) 1.58(2H, m), 1.79(2H, m), 2.46 (2H, m), 2.65(4H, m), 2.76(3H, s), 3.14(4H, m), 4.24 (2H, t, J=7.3Hz), 4.56(2H, s), 6.50(1H, d, J=3.0 Hz), 6.75(1H, d, J=3.0Hz), 6.87(2H, m), 6.96(2H, m), 9.76(1H, br.s) | (KBr) 2820, 1511, 1451, 1332, 1314, 1234, 1199, 1153, 1082, 982, 941, 824, 740, 704, 667 |
| 31 | (structure with pyrrole fused to S(O$_2$)-N(CH$_3$) six-membered ring, =NOH, (CH$_2$)$_3$N-piperazine-C$_6$H$_4$-F) | Colorless prism crystals 200.0–201.5° C. (ethyl acetate-hexane) | (270MHz) 2.02(2H, m), 2.42(2H, m), 2.65 (4H, m), 2.76(3H, s), 3.15(4H, m), 4.30(2H, t, J=6.6Hz), 4.55 (2H, s), 6.51(1H, d, J=2.6Hz), 6.77(1H, d, J=2.6Hz), 6.87(2H, m), 6.97(2H, m), 10.22(1H, br.s) | (KBr) 2832, 1736, 1509, 1460, 1326, 1232, 1198, 1151, 1083, 1010, 986, 943, 828, 759, 738, 716 |
| 32 | (structure with pyrrole fused to S(O$_2$)-N(CH$_3$) seven-membered ring, =NOH, (CH$_2$)$_3$N-piperazine-C$_6$H$_4$-F) | Colorless oil | (400MHz) 1.95(2H, m), 2.37(2H, t, J=7.0Hz), 2.57–2.68(4H, m), 2.81(3H, s), 3.06–3.21(6H, m), 3.61(2H, m), 4.15(2H, t, J=7.0Hz), 6.59(1H, d, J=2.9Hz), 6.69(1H, d, J=2.9Hz), 6.84–7.05(4H, m), 8.59(1H, br.s) | (film) 2826, 1510, 1328, 1236, 1192, 1147, 967, 737 |

*Measuring in CDCl$_3$ with TMS as an internal standard unless otherwise specifically indicated.

Tests

With respect to certain compounds of the present invention, their anti-$\alpha_1$ action and anti-serotonin (5-HT) action were investigated by the methods which will be described below. The results of some representative compounds are shown in Table 9.

(1) Anti-$\alpha_1$ Action

The thoracic aorta of each Hartley male guinea pig (body weight: 300–500 g) was excised. A preparation cut in a helical form was suspended under 1 g load in a Magnus cylinder filled with the Tyrode solution which had been aerated with a gas mixture of 95% $O_2$ and 5% $CO_2$ and maintained at 37° C. Using an isometric transducer ("TB-612J", manufactured by Nihon Kohden Corporation) and a pressure preamplifier ("AP-620G", manufactured by Nihon Kohden Corporation), variations in tension were measured. The isometric tensions were recorded on a thermal pen-writing recorder ("WT-647G", manufactured by Nihon Kohden Corporation). Taking the tonic contraction induced by $10^{-5}$ M norepinephrine (NE) as 100%, the percent contractions upon addition of each test drug at $10^{-8}$ M and $10^{-7}$ M were determined and recorded as $\alpha_1$ action.

(2) Anti-serotonin (5-HT) Action

The superior mesenteric artery of each Hartley male guinea pig (body weight: 300–500 g) was excised. A preparation cut in a helical form was suspended under resting tension of 0.3 g in a Magnus cylinder filled with the Tyrode solution which had been aerated with a gas mixture of 95% $O_2$ and 5% $CO_2$ and maintained at 37° C. Using an isometric transducer ("UL-10", manufactured by SHINKOH K.K.) and a pressure preamplifier ("DSA-605A", manufactured by SHINKOH K.K.), variations in tension were measured. The isometric tensions were recorded on a pen-writing recorder ("VP-6537A", manufactured by NATIONAL K.K.). Taking the contraction induced by $10^{-5}$ M serotonin (5-HT) as 100%, the percent contractions by $10^{-5}$ M 5-HT in the presence of each test drug at $10^{-7}$ M and $10^{-6}$ M were determined as anti-5-HT action.

(3) Results

TABLE 9

| Comp'd No. | Anti 5-HT action (% of Control) | | Anti $\alpha_1$ action (% of Control) | |
|---|---|---|---|---|
| | $10^{-7}$ M | $10^{-6}$ M | $10^{-8}$ M | $10^{-7}$ M |
| 22 | 80.4 | 41.1 | 66.6 | 43.2 |
| 26 | 95.5 | 47.5 | 95.2 | 55.6 |
| 28 | 73.5 | 30.2 | 80.0 | 45.8 |
| 29 | 79.0 | 32.5 | 83.1 | 33.4 |

Capability of Exploitation in Industry

The pyrrolesulfonamide compounds (I) and their salts according to the present invention have strong $\alpha_1$-blocking action and serotonin-2 blocking action. Accordingly, the present invention has made it possible to provide preventives and therapeutics for all circulatory diseases such as hypertension, heart failure, ischemic heart diseases, cerebrovascular disturbances and peripheral circulatory disturbances.

What is claimed is:

1. A compound represented by the following formula (XVI):

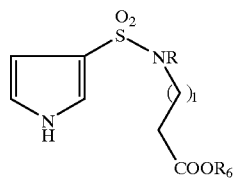

(XVI)

wherein R represents a hydrogen atom, a linear or branched alkyl group, a cycloalkyl group, a cycloalkylalkyl group or a substituted or unsubstituted aralkyl group, $R_6$ represents a hydrogen atom or a carboxyl-protecting group and l represents 0 or 1.

2. A compound represented by the following formula (XIII):

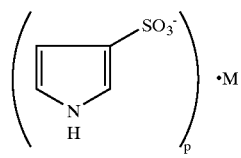

(XIII)

wherein M represents a hydrogen ion, an alkali metal ion, an alkaline earth metal ion or a quaternary ammonium ion, and p stands for 1 when M represents a hydrogen ion, an alkali metal ion or a quaternary ammonium ion or p stands for 2 when M represents an alkaline earth metal ion.

3. A compound according to claim 2, wherein in the formula (XIII), M is a sodium ion and p is 1.

4. A process for the preparation of a compound represented by the following formula (XIII):

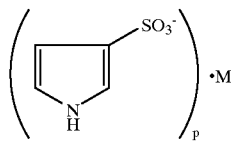

(XIII)

wherein M represents a hydrogen ion, an alkali metal ion, an alkaline earth metal ion or a quaternary ammonium ion, and p stands for 1 when M represents a hydrogen ion, an alkali metal ion or a quaternary ammonium ion or p stand for 2 when M represents an alkaline earth metal ion, which comprises treating pyrrole with sulfur trioxide-pyridine complex and treating the resultant compound with a corresponding acid or base when M is other than a hydrogen ion.

5. A process for the preparation of a compound represented by the following formula (XIIIa):

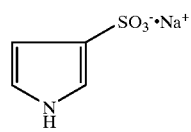

(XIIIa)

which comprises treating pyrrole with sulfur trioxide pyridine complex and then treating the resultant compound with sodium carbonate, sodium hydrogencarbonate or sodium hydroxide.

* * * * *